(12) United States Patent
Kia et al.

(10) Patent No.: US 10,245,023 B2
(45) Date of Patent: Apr. 2, 2019

(54) SUTURE DEVICE

(71) Applicants: Michael Amirfarzad Kia, Grand Blanc, MI (US); Frank Bonadio, Bray (IE); Lucy Dolores Halpin, Dublin (IE)

(72) Inventors: Michael Amirfarzad Kia, Grand Blanc, MI (US); Frank Bonadio, Bray (IE); Lucy Dolores Halpin, Dublin (IE)

( * ) Notice: Subject to any disclaimer, the term of this patent is extended or adjusted under 35 U.S.C. 154(b) by 1 day.

(21) Appl. No.: 15/026,028

(22) PCT Filed: Oct. 1, 2014

(86) PCT No.: PCT/US2014/058638
§ 371 (c)(1),
(2) Date: Mar. 30, 2016

(87) PCT Pub. No.: WO2015/050999
PCT Pub. Date: Apr. 9, 2015

(65) Prior Publication Data
US 2016/0242763 A1 Aug. 25, 2016

Related U.S. Application Data

(60) Provisional application No. 61/885,904, filed on Oct. 2, 2013.

(51) Int. Cl.
*A61B 17/04* (2006.01)
*A61F 2/00* (2006.01)
(Continued)

(52) U.S. Cl.
CPC ...... *A61B 17/0469* (2013.01); *A61B 17/0467* (2013.01); *A61B 17/0482* (2013.01);
(Continued)

(58) Field of Classification Search
CPC .... A61F 2/0063; A61F 2002/0068–2002/0072
See application file for complete search history.

(56) References Cited

U.S. PATENT DOCUMENTS

| 4,440,171 A | 4/1984 | Nomoto et al. |
| 5,417,700 A | 5/1995 | Egan |

(Continued)

FOREIGN PATENT DOCUMENTS

| WO | WO-0134035 A1 | 5/2001 |
| WO | WO-2010/138580 A2 | 12/2010 |
| WO | WO-2010/138580 A3 | 5/2011 |

OTHER PUBLICATIONS

Preliminary Report on Patentability for PCT/US2014/058638, dated Apr. 14, 2016.
(Continued)

*Primary Examiner* — Shaun David
(74) *Attorney, Agent, or Firm* — Harness, Dickey & Pierce, P.L.C.

(57) ABSTRACT

A suture device comprises a shaft and a needle which creates a curved pathway for delivery of a suture. The curved needle is rotatably movable from a retracted to an extended configuration. The suture is housed in a feed channel within the shaft. The shaft also houses a suture receiving channel with an open distal end. A suture cutter is located adjacent to the suture feed channel distal end for cutting the suture, when required. The device also comprises a rotatable twisting element having a rotating shaft and a pair of radially extending arms, having through suture-receiving through holes. A heating rod in the form of a heating element is also provided to heat meld a twist when formed in the suture.

12 Claims, 27 Drawing Sheets

(51) Int. Cl.
*A61B 17/06* (2006.01)
*A61B 17/00* (2006.01)

(52) U.S. Cl.
CPC .... *A61B 17/0491* (2013.01); *A61B 17/06166* (2013.01); *A61F 2/0063* (2013.01); *A61B 17/0493* (2013.01); *A61B 2017/003* (2013.01); *A61B 2017/0619* (2013.01); *A61B 2017/06052* (2013.01)

(56) References Cited

U.S. PATENT DOCUMENTS

| | | | |
|---|---|---|---|
| 5,860,992 | A | 1/1999 | Daniel et al. |
| 6,786,913 | B1 | 9/2004 | Sancoff et al. |
| 2002/0116010 | A1 | 8/2002 | Chung et al. |
| 2004/0087979 | A1* | 5/2004 | Field ............... A61B 17/0469 606/148 |
| 2004/0092969 | A1 | 5/2004 | Kumar |
| 2005/0049638 | A1 | 3/2005 | Mandelbaum |
| 2008/0172071 | A1 | 7/2008 | Barker |
| 2011/0015760 | A1* | 1/2011 | Kullas ............... A61F 2/0063 623/23.72 |
| 2011/0208320 | A1* | 8/2011 | Stevenson ............ A61B 17/08 623/23.72 |
| 2011/0270279 | A1 | 11/2011 | Badhwar |
| 2013/0158568 | A1 | 6/2013 | Kia et al. |

OTHER PUBLICATIONS

European Search Report for Application No. EP14850216.4—1664/3062710 dated May 15, 2017 (12 pages).

\* cited by examiner

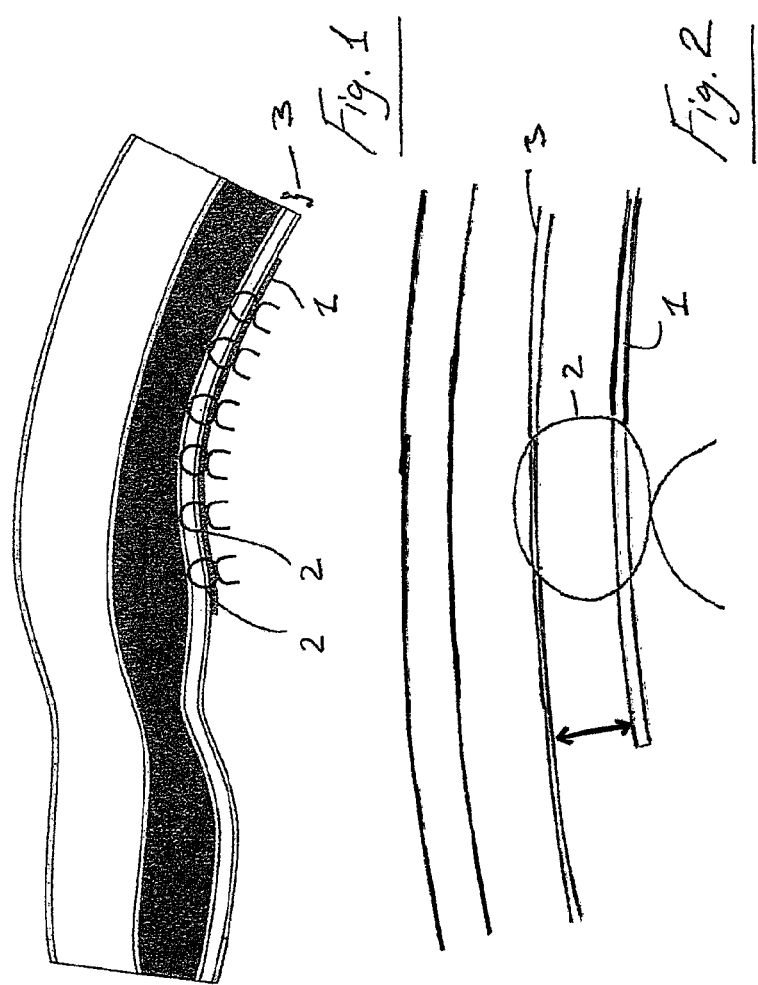

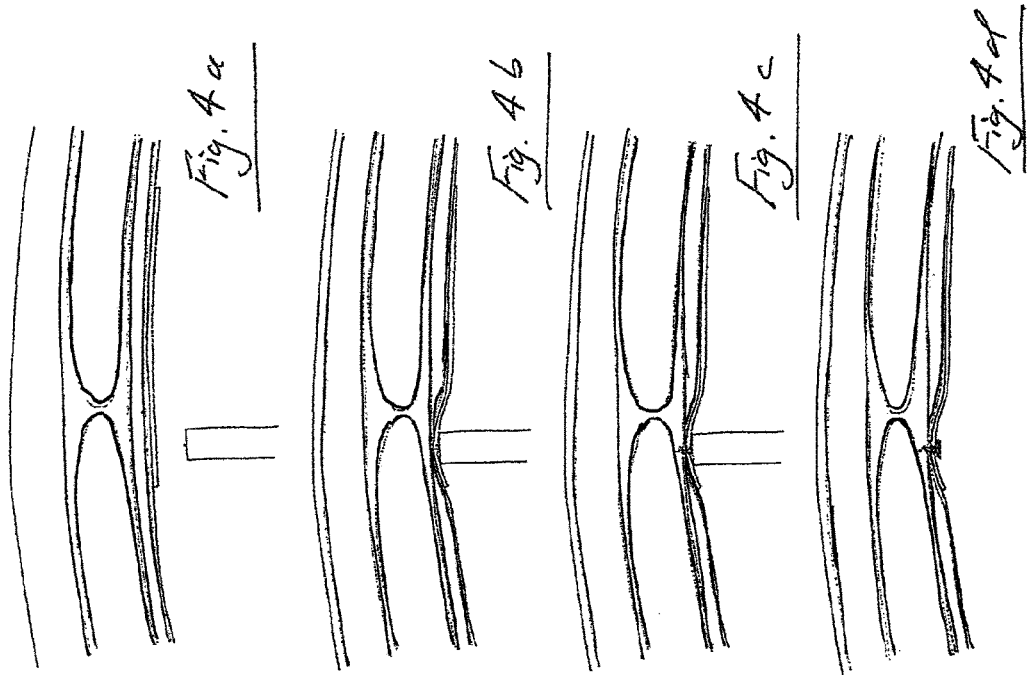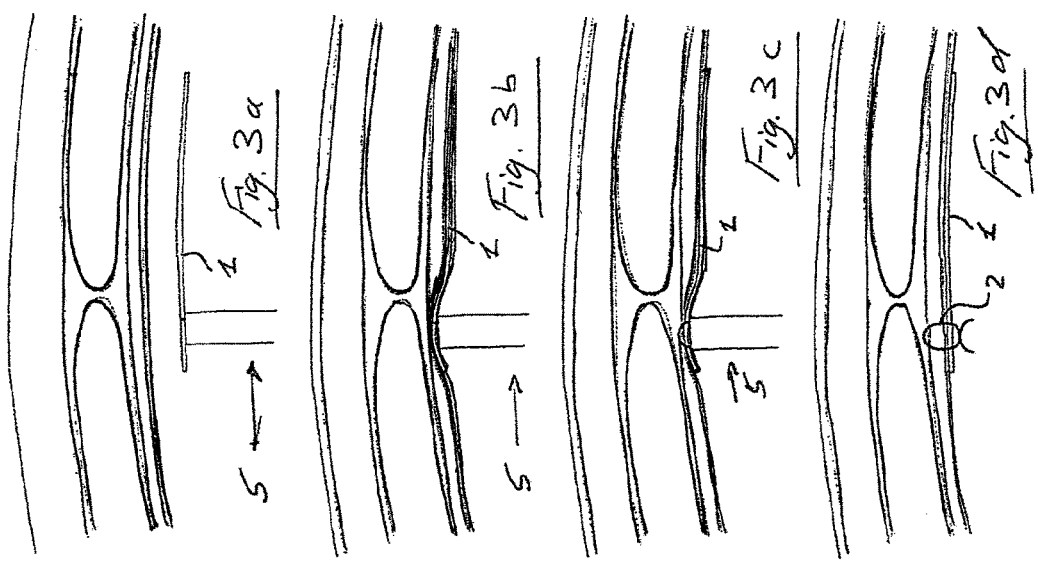

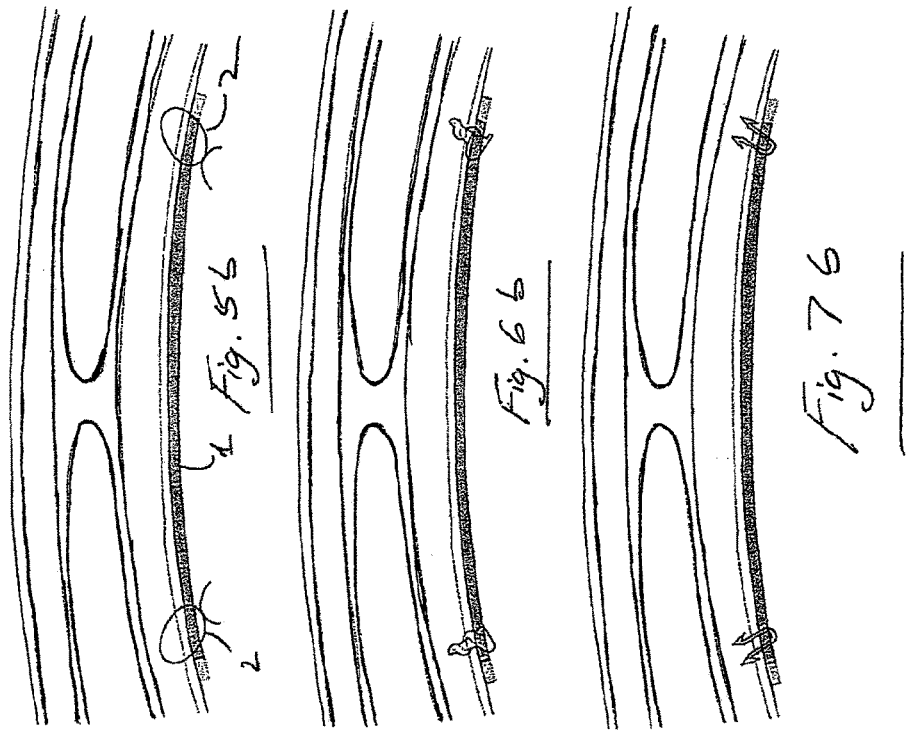
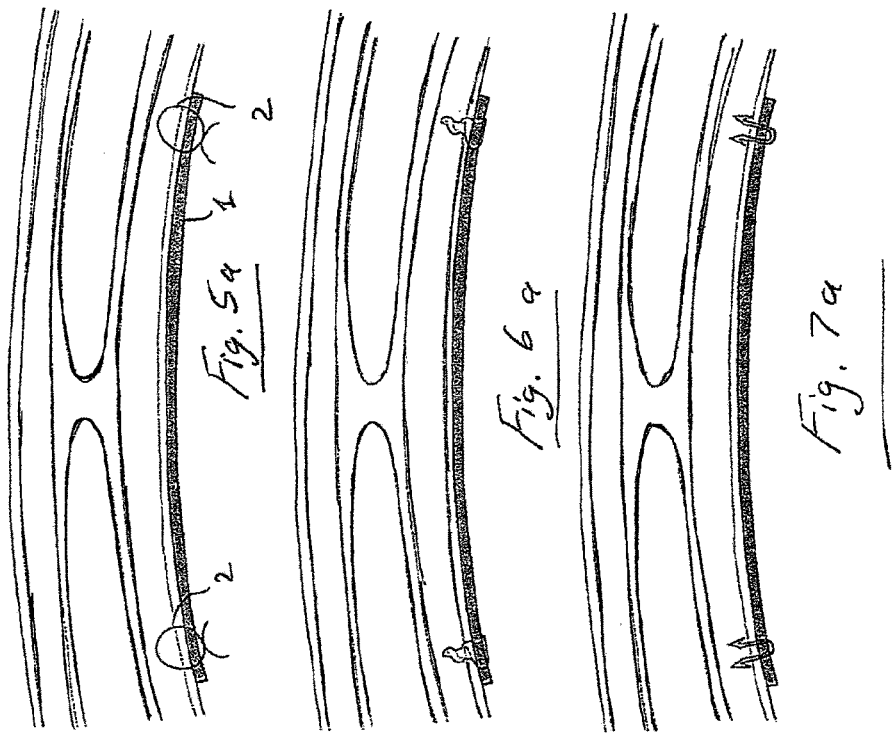

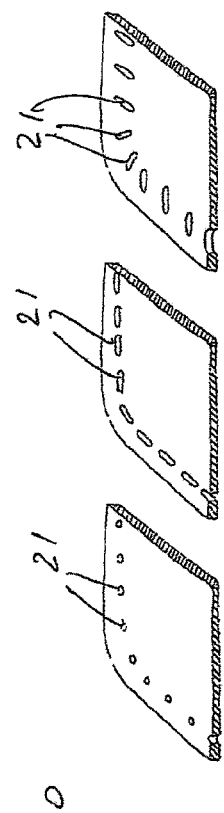
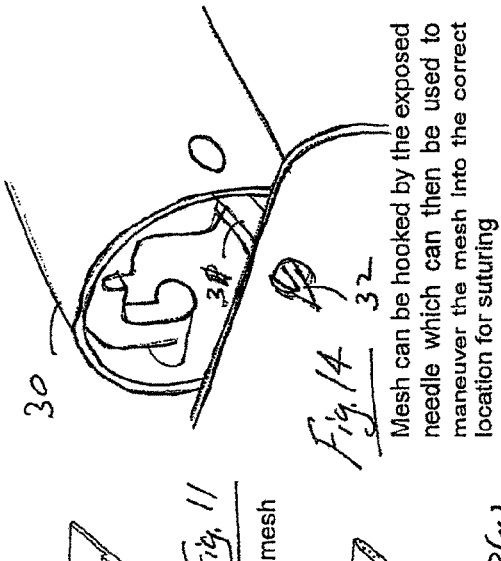
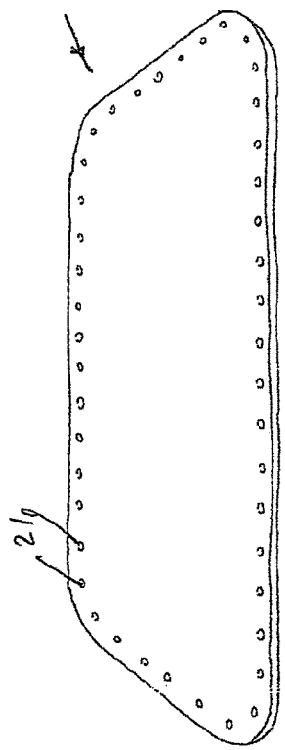
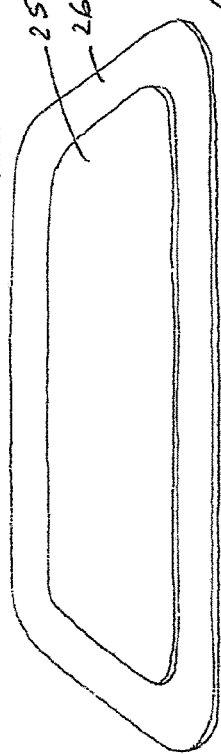
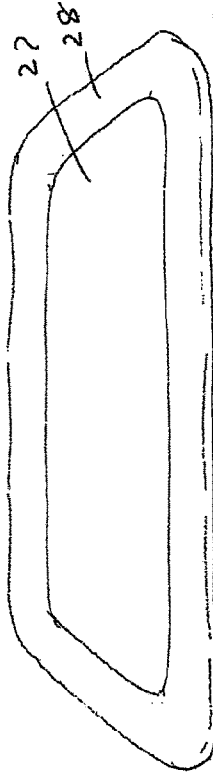

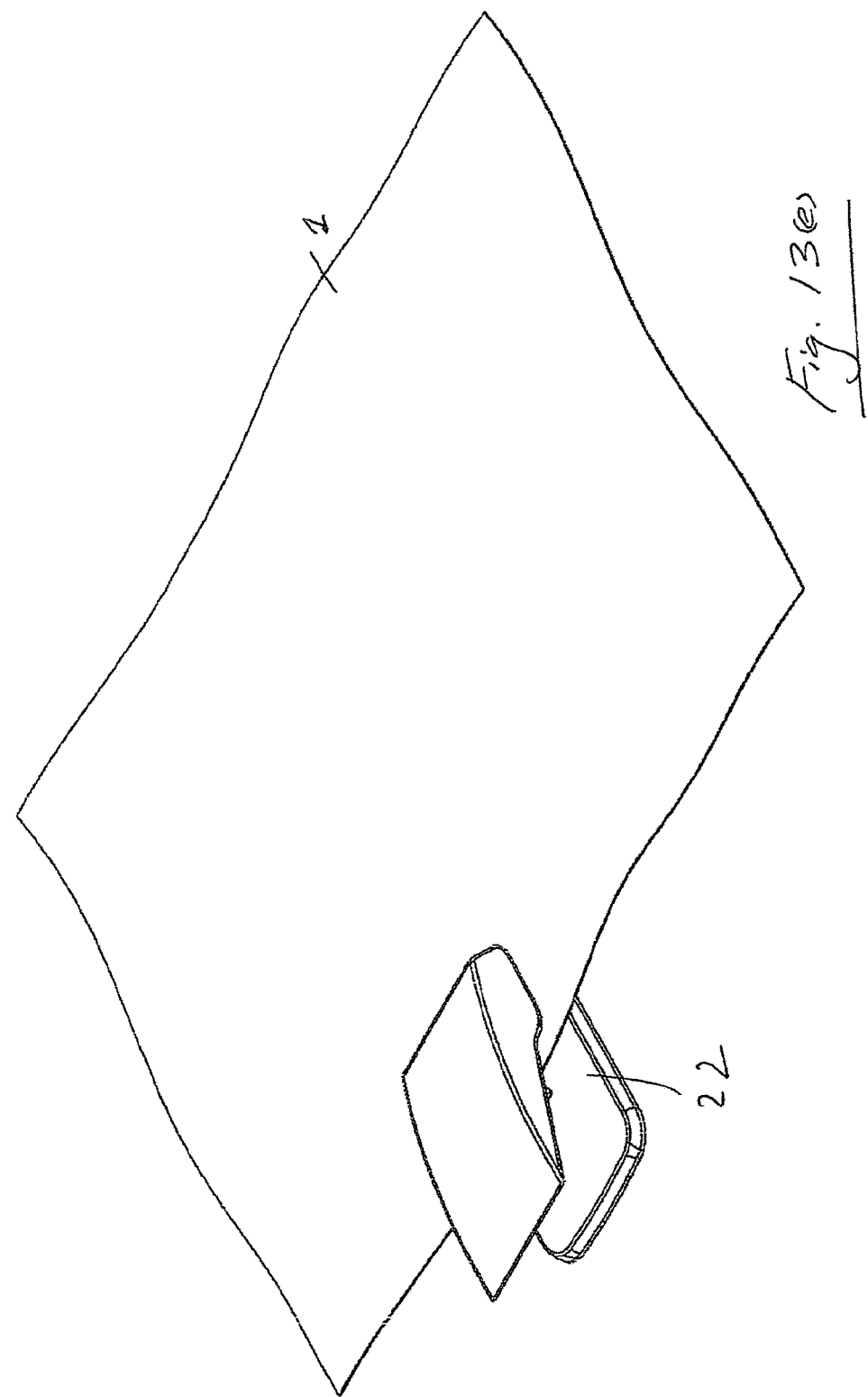

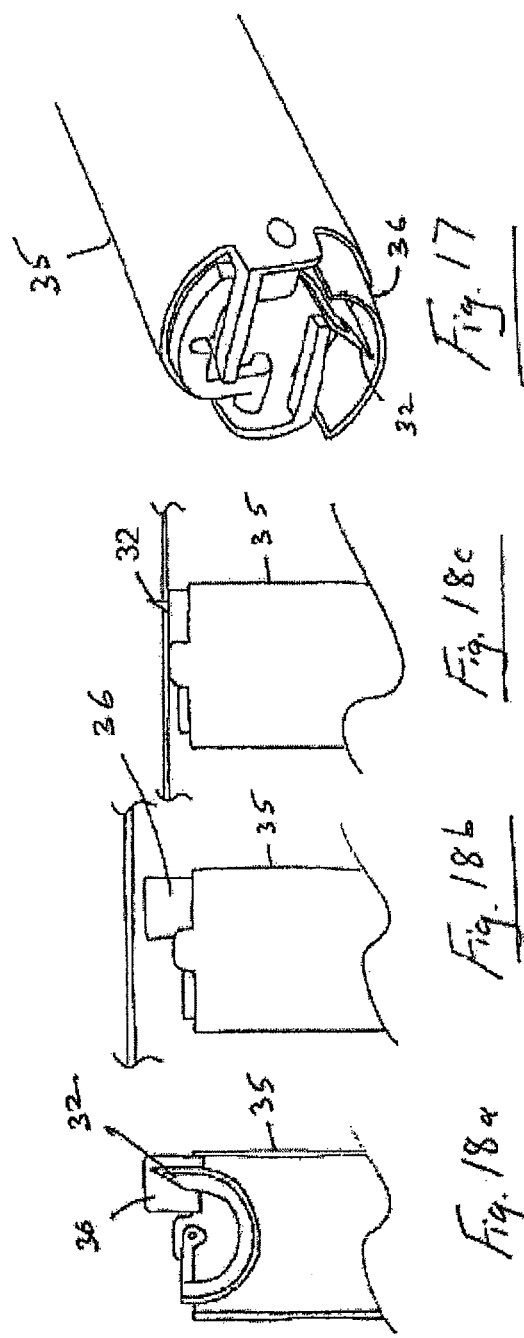

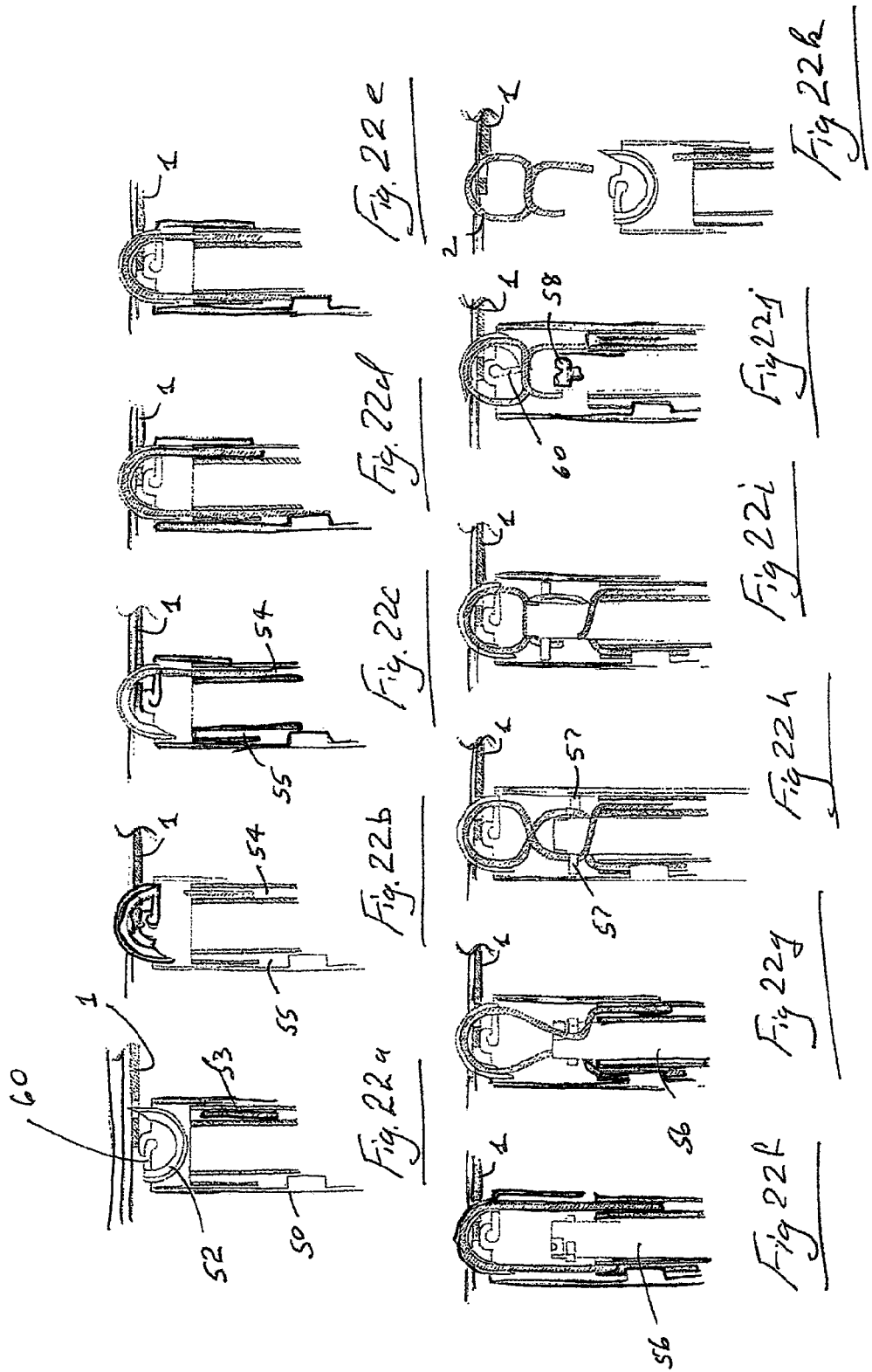

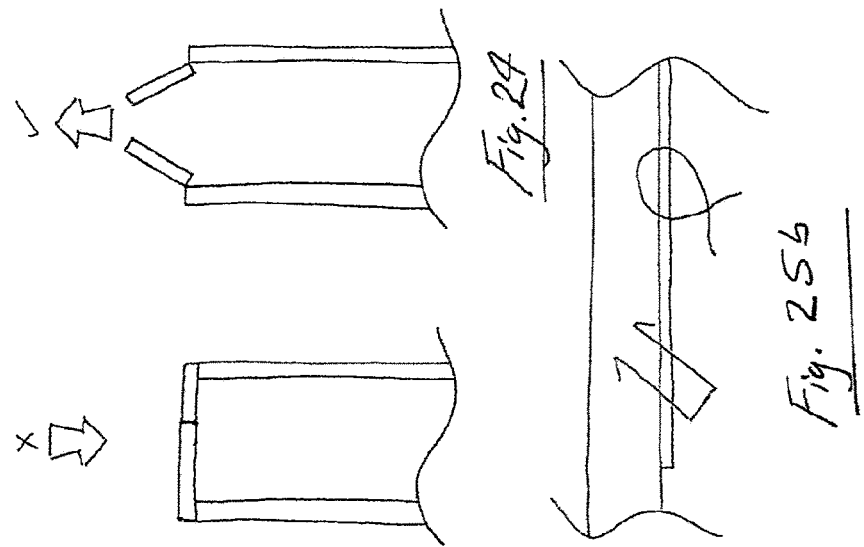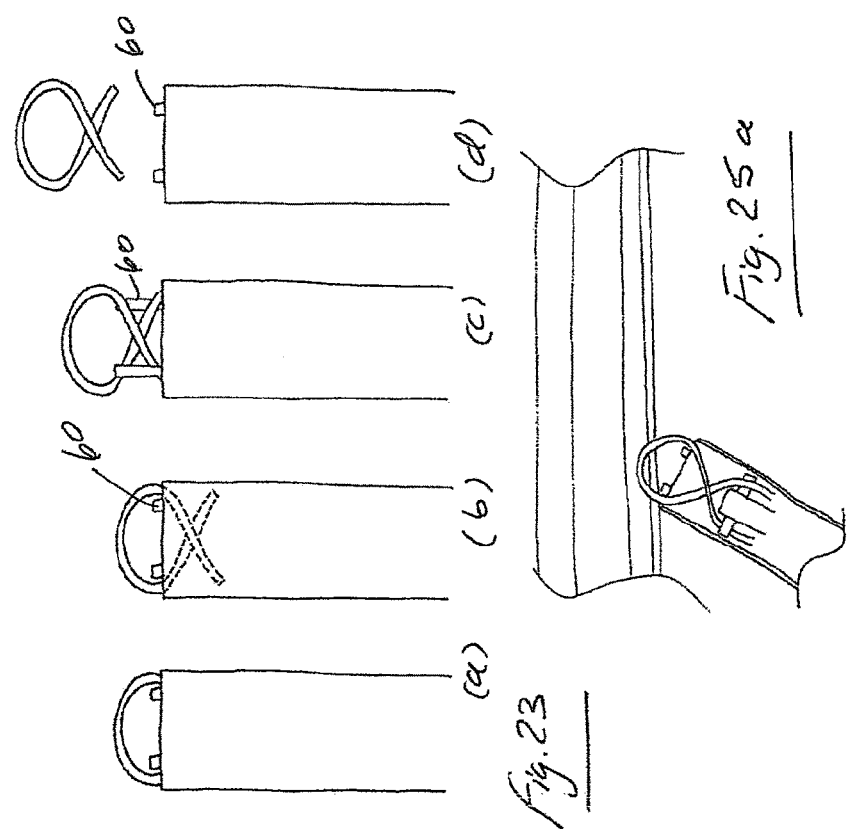

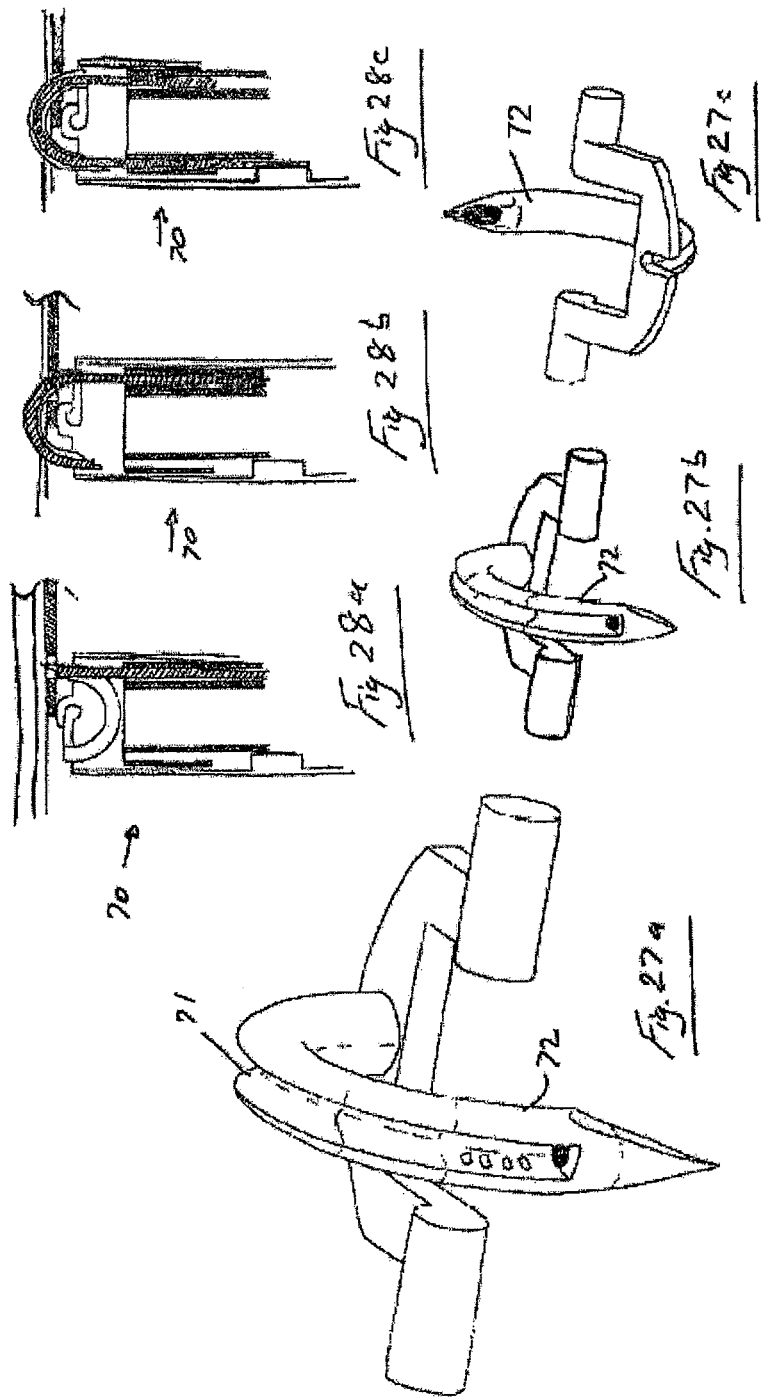

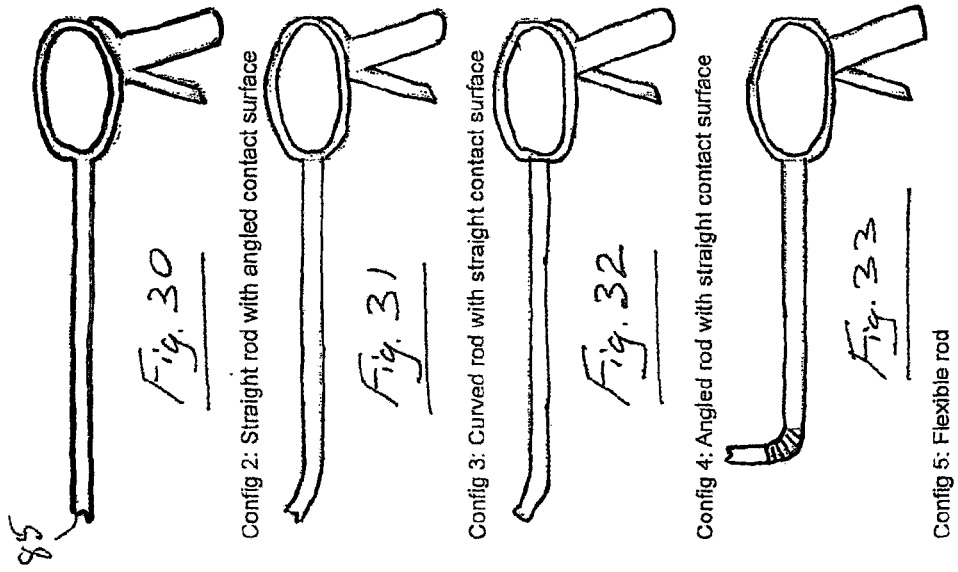
Fig. 30 — Config 2: Straight rod with angled contact surface
Fig. 31 — Config 3: Curved rod with straight contact surface
Fig. 32 — Config 4: Angled rod with straight contact surface
Fig. 33 — Config 5: Flexible rod
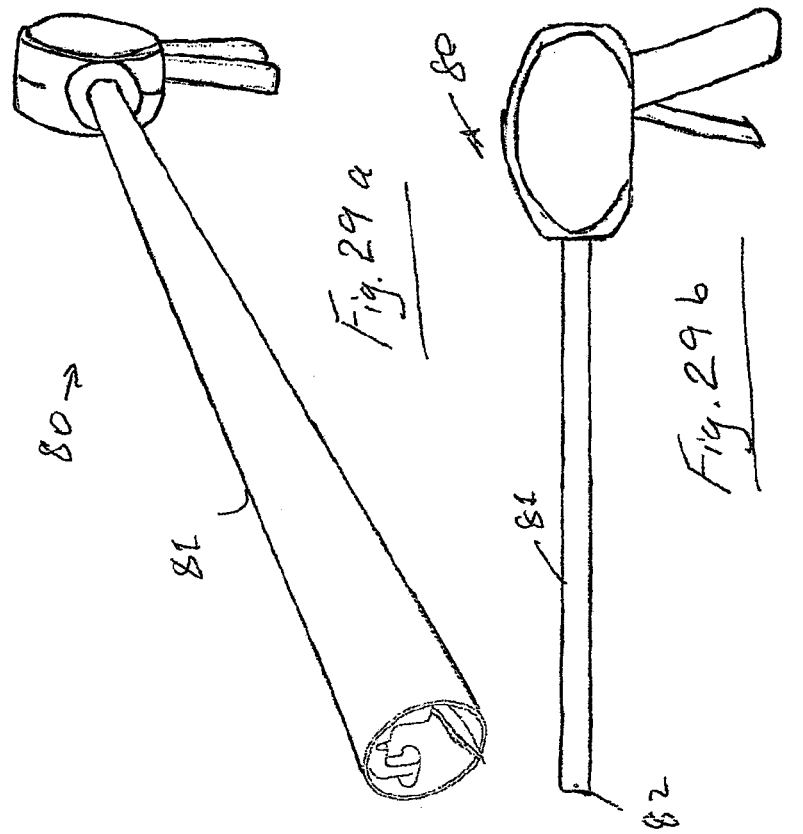
Fig. 29a
Fig. 29b — Config 1: Straight rod with straight contact surface Config 7: Flexible option for use in the stomach or colon Config 6: Distal end of the device can rotate independently

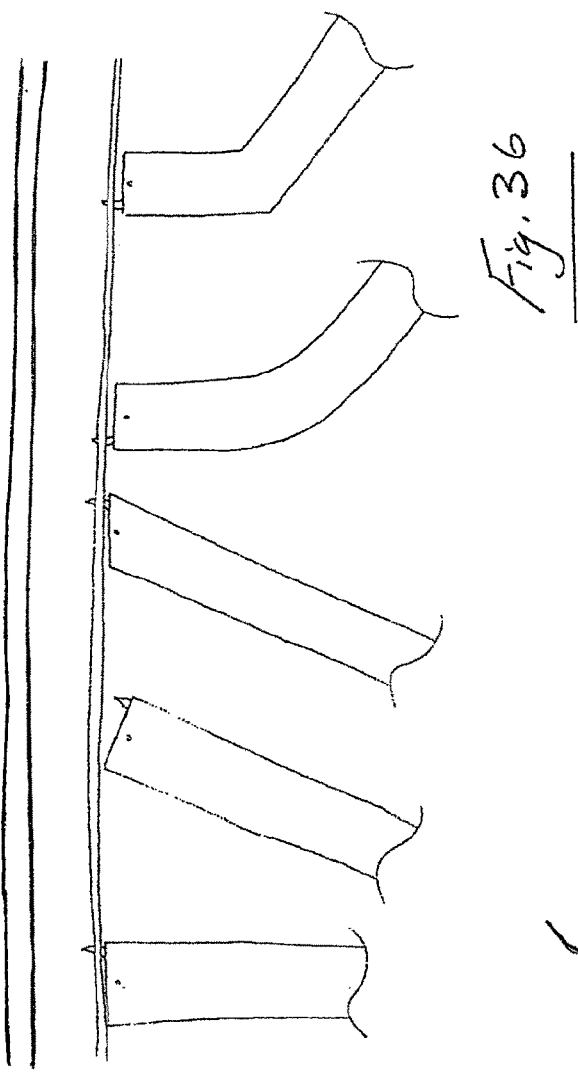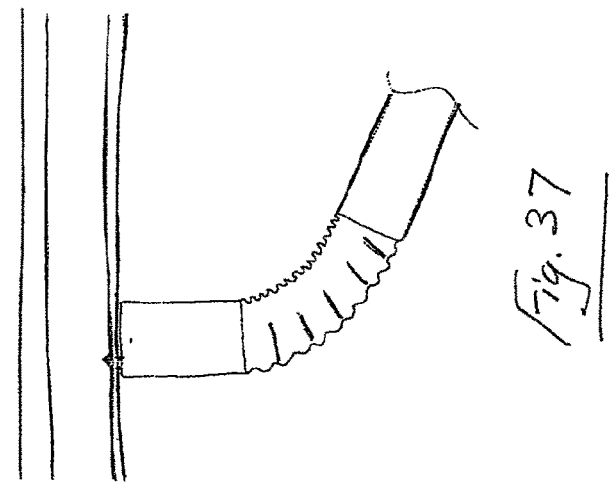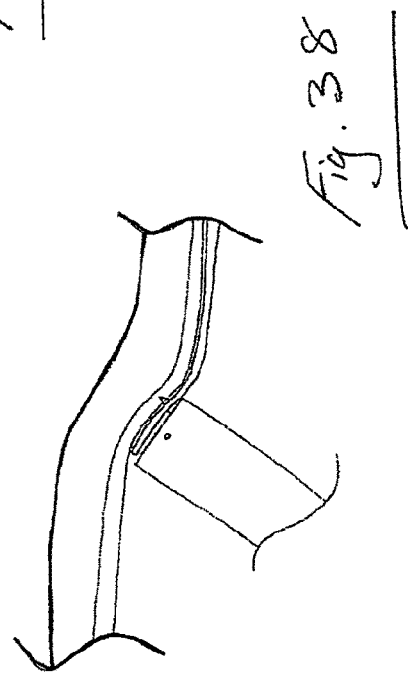

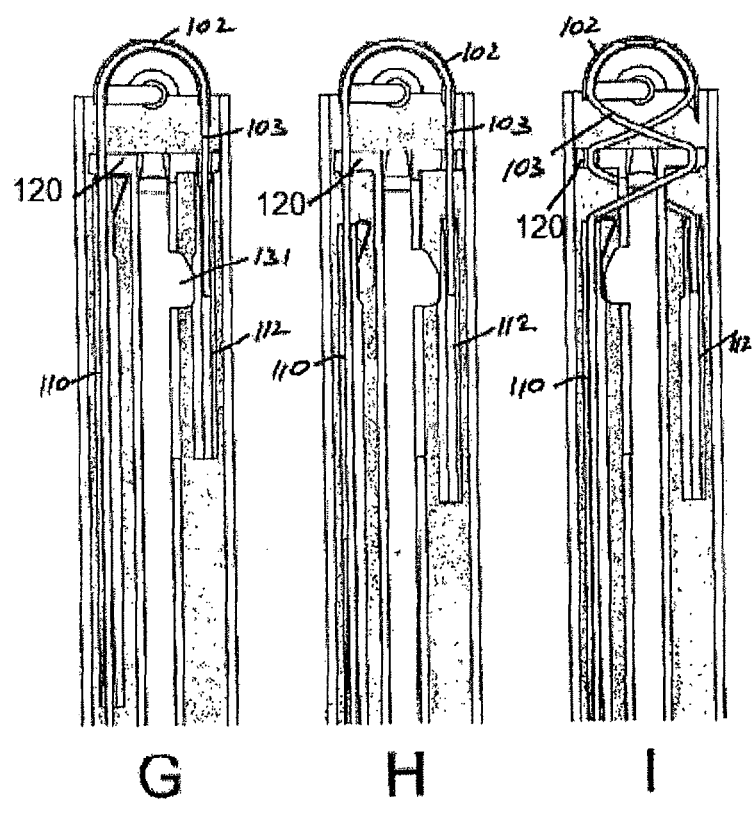
Fig. 40 Contd.

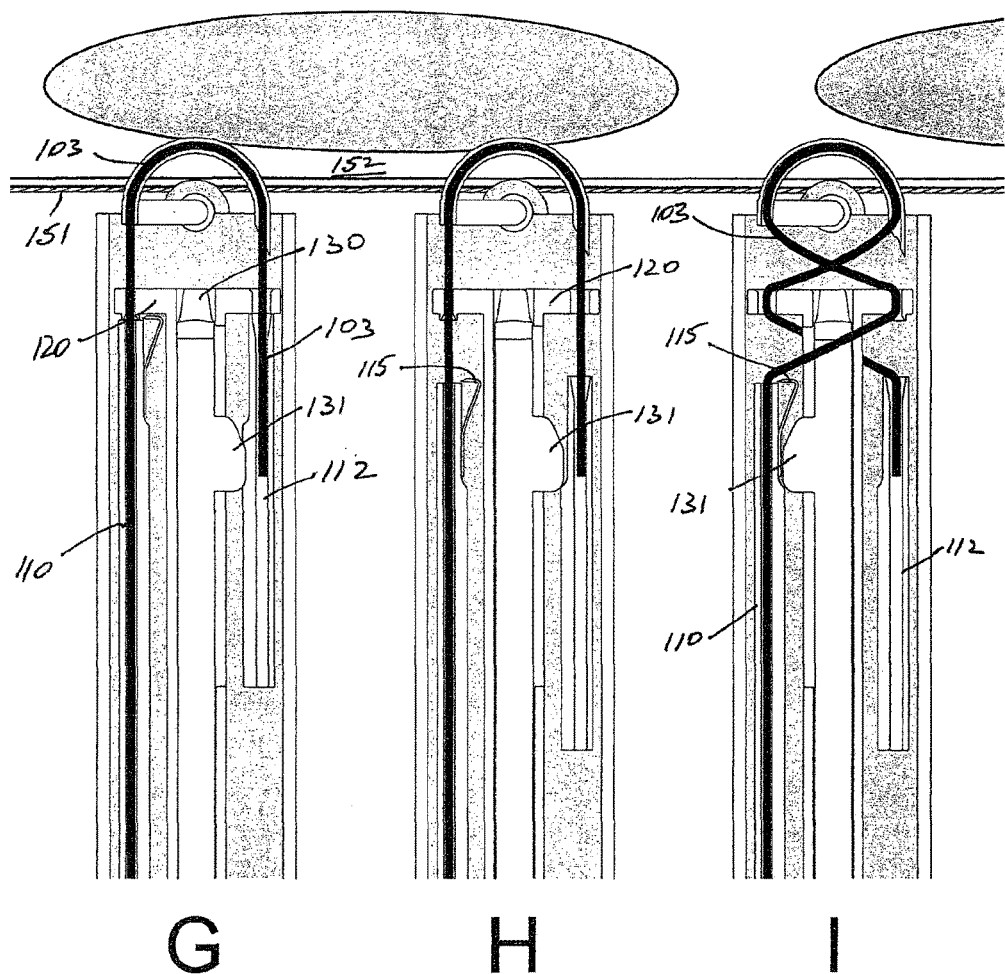
Fig. 41 contd.

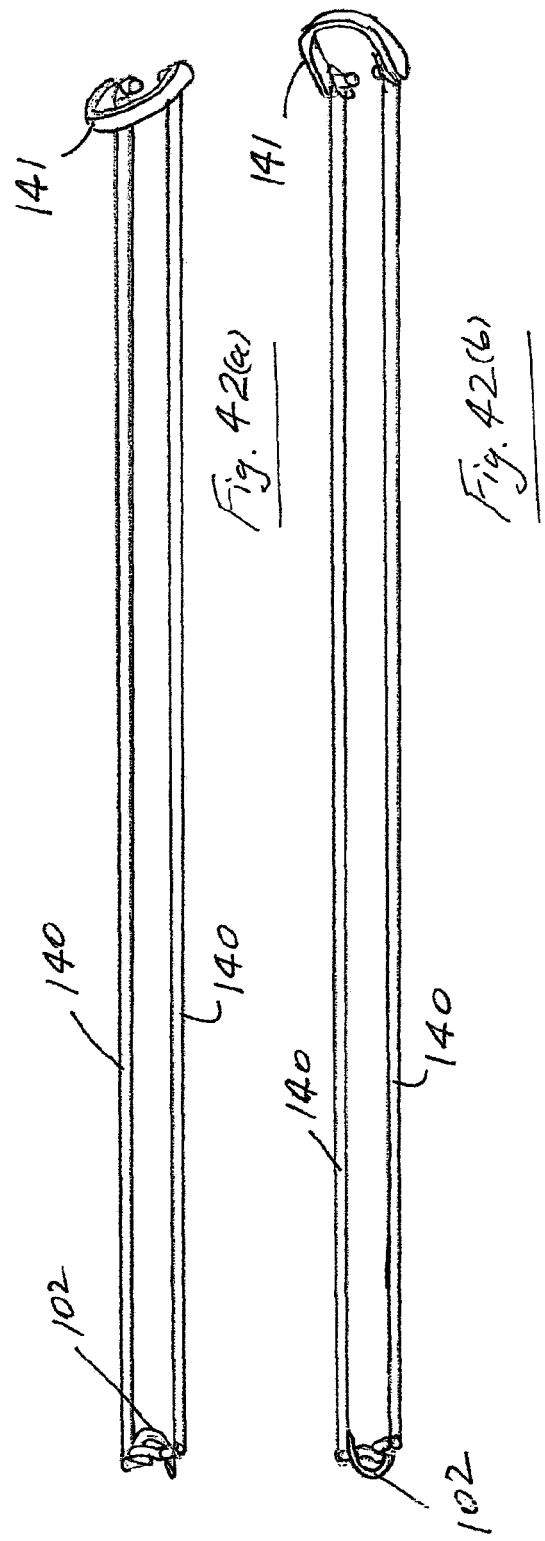

SUTURE DEVICE

CROSS-REFERENCE TO RELATED APPLICATIONS

This application is a 371 U. S. National Stage of International Application No. PCT/US2014/058638, filed on Oct. 1, 2014 and claims priority to U.S. Provisional application 61/885,904 filed on Oct. 2, 2013. The entire disclosures of the above applications are incorporated herein by reference.

The invention relates to a device and a system for hernia repair.

INTRODUCTION

A hernia is a development of a gap in the connective tissue of the abdominal wall. One type of hernia is a ventral hernia that can form in the linea alba region of the body. In such hernias often a weakness develops in the abdominal wall that contains the intestine. Part of the intestine pushes into the weakened area and can become restricted leading to digestive complications and pain.

To repair such hernias usually a mesh is used to bridge the weakened area in the abdominal wall. Such ventrical hernia repair procedures can be carried out either using open surgery or closed laparoscopic surgery.

In open surgery procedures an open incision is made and a synthetic or biological mesh is used to bridge the gap. The mesh is secured in position using standard suturing techniques. Generally in such open surgical procedures the mesh is sewn with sutures which are not biologically absorbable.

In conventional laparoscopic hernia repair procedures a mesh is secured in position using tacks which are delivered laparoscopically and/or transfascial sutures are used which are delivered transabdominally. Such transabdominal suturing techniques are however time consuming and can be technically challenging. The sutures and the associated tacks can cause significant patient discomfort and pain. The rate of subsequent infection after laparoscopic hernia repair is substantially less than in open surgery. The recovery time is also much faster than for open surgery hernia repair.

An object of the invention is to provide devices and systems for improved laparoscopic hernia repair.

STATEMENTS OF INVENTION

According to the invention there is provided a suture device comprising a shaft, a needle at the distal end of the shaft to create a curved pathway for delivery of a suture through portion of an internal body wall and a closure device for closing the suture to form a loop.

In one embodiment the needle is movable from a retracted configuration at least partially within the shaft to an extended configuration for passing through portion of an internal body wall. In one case the needle is rotatably movable between the retracted and the extended configuration.

In one embodiment the needle has a distal tip which projects from the distal end of the shaft.

In this case the device may comprise a retractable shroud for the projecting distal tip of the needle.

In one embodiment the needle is of arcuate shape.

In one case the needle comprises an open suture-receiving channel. The suture-receiving channel may be of generally U-shaped in transverse cross section.

In one embodiment the device comprises a proximal handle for controlling movement of the needle. There may be operating elements extending between the proximal handle and the needle.

The suture device may comprise a rotary device for twisting the suture to form a loop.

The suture device may comprise a heating device for fusing the suture.

The suture device may comprise a cutting device for cutting the suture.

In one embodiment the device comprises a suture feed channel for delivering a suture to the needle. The device may also comprise a suture return channel for receiving a suture delivered through the needle.

In one embodiment the suture device comprises a rotary device for twisting the suture to form a loop, the twisting device having a suture receiving hole and a suture return hole, the rotary device being rotatable from a receiving configuration in which the suture receiving hole and the suture return hole are in alignment with the suture feed channel and the suture return channel respectively to a twisted configuration in which the suture receiving hole and the suture return hole are in alignment with the suture return channel and the suture feed channel respectively.

In one embodiment the suture return channel has an opening at the distal end which is larger than an opening at the distal end of the suture feed channel.

In one case the suture device further comprises a fusing element for fusing a twist in a suture. The device may also comprise a suture cutting element for cutting the twisted suture. The fusing element may be movable from a retracted to an advanced configuration. In one case the cutting element is activated on movement of the fusing element from the retracted to the advanced configuration.

In one embodiment the needle is mounted to an arm which is rotatably mounted to the shaft. The device may comprise an operating system for the needle arm. The operation system comprises operating elements extending from the needle arm to the proximal end of the shaft. The device may comprise a proximal handle for controlling the movement of the needle from the proximal end of the shaft.

In one embodiment the suture device comprises a retainer or bridge for stabilising the suture during cutting and/or fusing.

In some embodiments at least a portion of the shaft is adjustable.

At least a portion of the shaft is flexible and/or malleable.

In one case at least a portion of the shaft is rotatable.

In one embodiment the shaft comprises at least one bend.

In the invention an automated suturing mechanism involves passing a suture through a hollow curved needle to secure a mesh to the abdominal wall. The suture will be welded/fused to form a bond, for example, using a grooved heating element.

In one embodiment, the device will contain a rotational heating shaft that will be used to create an overlap of suture. The rotational heating element will function to capture the two strands of the suture and create an overlap to allow for suture welding. The rotational element may have wing(s) that can capture the suture strands within the shaft of the device. The wing may be offset from a center channel of the heating element.

In one embodiment the heating element may press the suture against the mesh to serve as a endplate for welding the mesh.

In one embodiment the device will have an outer shaft and inner shaft that will be able to move independently. The inner shaft may contain the suture strands within closed or partially open channels. Movement of the inner shaft may be used to expose the suture for the rotational element.

In one embodiment the inner shaft may rotate to create a crossing of the suture strands.

In another embodiment the inner shaft may move to a position to carry the distal ends of the suture loop to a point perpendicular to the heating element to allow for suture welding.

In another embodiment the retraction of the inner shaft may be used to facilitate locking of the distal tail of the suture.

In one embodiment the end effector on the outer or inner shaft will have bridges to limit collapse of the suture loop. This will ensure that every loop is of the same diameter independent of the material within the loop.

In one case the bridges will cause predictable alignment of the suture strands in front of the heating element (for example, perpendicularly).

In another embodiment the bridge on the end effector will limit the tension on the tissue caught in the suture loop.

In another embodiment the suture used in the device may comprise three layers of progressively increasing melting temperature from the outside to the inside.

In another embodiment the mesh that may be used with this device will have precut perforations in the edges to allow for penetrance of the needle. These precut perforations will be marked for identification. The perforations may be linear, circular, or other shape and may be located at variable distances to allow for proper function for fixation.

The invention also provides a hernia repair mesh having a plurality of holes provided therein to receive a suture.

In one embodiment the suture receiving holes are provided around at least a portion of the periphery of the mesh.

Also provided is a hernia repair mesh having a main mesh body and a peripheral portion surrounding the main mesh body, the peripheral portion being adapted for reception of sutures. In one case the peripheral portion is softer with respect to the main mesh body.

Alternatively or additionally the peripheral portion is of reduced thickness with respect to the main mesh body.

In one embodiment the hernia repair mesh comprises a plurality of holes to receive individual sutures.

In another aspect the invention provides a hernia repair system and a mesh as described.

In yet another aspect of the invention provides a method for repairing a hernia comprising the steps of:—
   providing a suture device;
   providing a mesh;
   laparoscopically delivering the mesh to the site of the hernia;
   delivering the suture device to the site of the hernia; and
   laparoscopically suturing the mesh to an internal body wall at the site of the hernia.

In one embodiment the step of suturing the mesh comprises suturing a plurality of individual sutures to an internal body wall at the site of the hernia.

In one embodiment the suture comprises a closed loop which extends through the mesh, into the body wall and out of the body wall.

In one case the loop is adapted to facilitate movement of the mesh relative to the body wall.

BRIEF DESCRIPTION OF THE DRAWINGS

The invention will be more clearly understood from the following description thereof, given by way of example only, in which:

FIG. 1 is a cross sectional view of an abdomen wall with a hernia repair mesh and associated sutures according to the invention;

FIG. 2 is an enlarged view illustrating a single suture;

FIGS. 3a to 3d illustrate steps used in a hernia repair method of the invention;

FIGS. 4a to 4d illustrate steps in a tacking system for conventional hernia repair;

FIGS. 5a and 5b illustrate hernia repair using the system of the invention;

FIGS. 6a and 6b illustrate conventional hernia repair using one type of tacking system;

FIGS. 7a and 7b illustrate conventional hernia repair using another type of tacking system;

FIGS. 8 and 9(a) to 9(c) illustrate the use of the mesh of the invention;

FIGS. 10 and 11 illustrate another mesh of the invention;

FIGS. 12 and 13(a) illustrate a further mesh of the invention;

FIGS. 13(b) to 13(e) illustrate further meshes;

FIGS. 14 to 16 illustrate the distal end of a suture device of the invention engaging a mesh;

FIG. 17 shows the distal end of another suture device of the invention;

FIGS. 18a to 18c are views illustrating the suture device of FIG. 17, in use;

FIGS. 22a to 22k are cross sectional views of a suture device according to the invention in various configurations of use;

FIGS. 23a to 23d are views of a detail of the suture device, in use;

FIG. 24 shows another detail of a suture device;

FIGS. 25a and 25b illustrate one method of use of the suture device;

FIGS. 27a to 27c illustrate a further suture device of the invention;

FIGS. 28a to 28c show the device of FIG. 26, in use;

FIGS. 29a and 29b illustrate one form of suture device according to the invention;

FIGS. 30 to 33 illustrate alternate forms of suture devices of the invention;

FIGS. 36 to 38 show various types of suture devices according to the invention, in use;

FIGS. 42a and b illustrate a suture needle operating system.

DETAILED DESCRIPTION

Figure 13B:
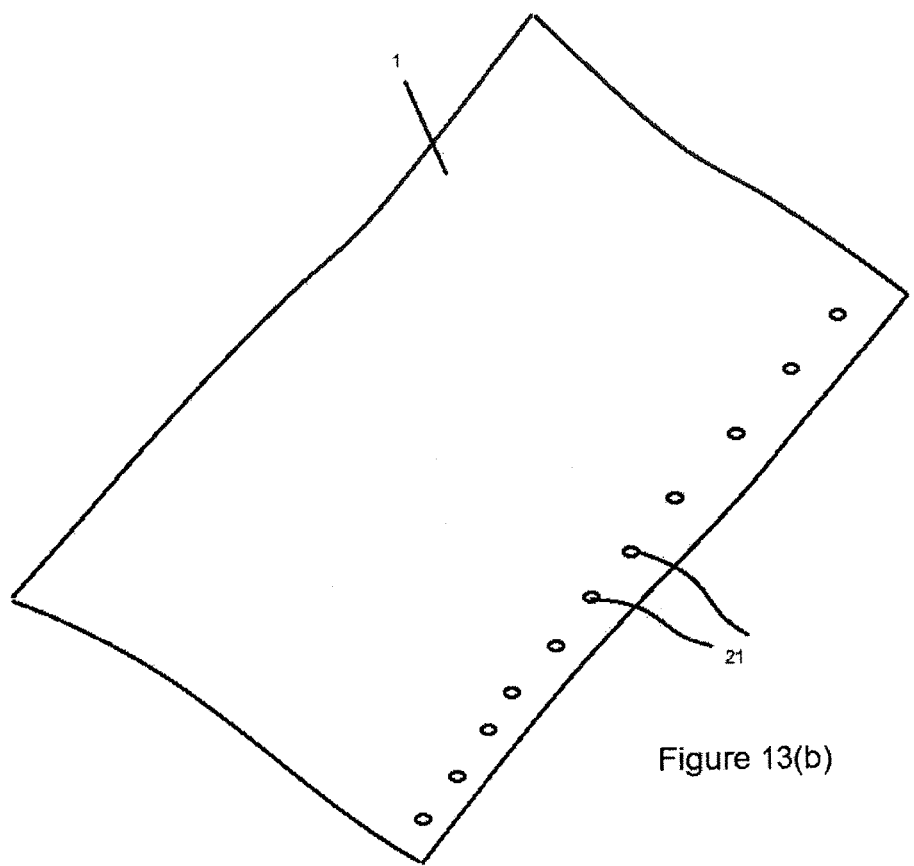
Figure 13C:
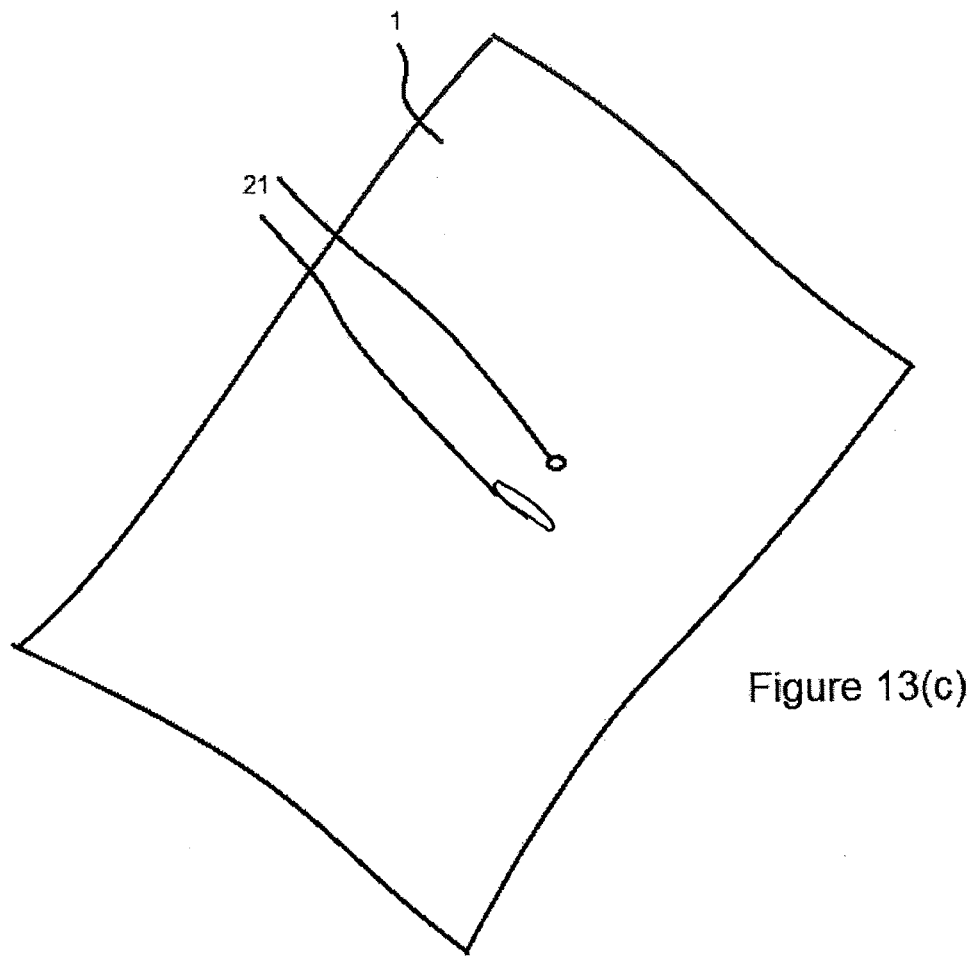
Figure 13D:
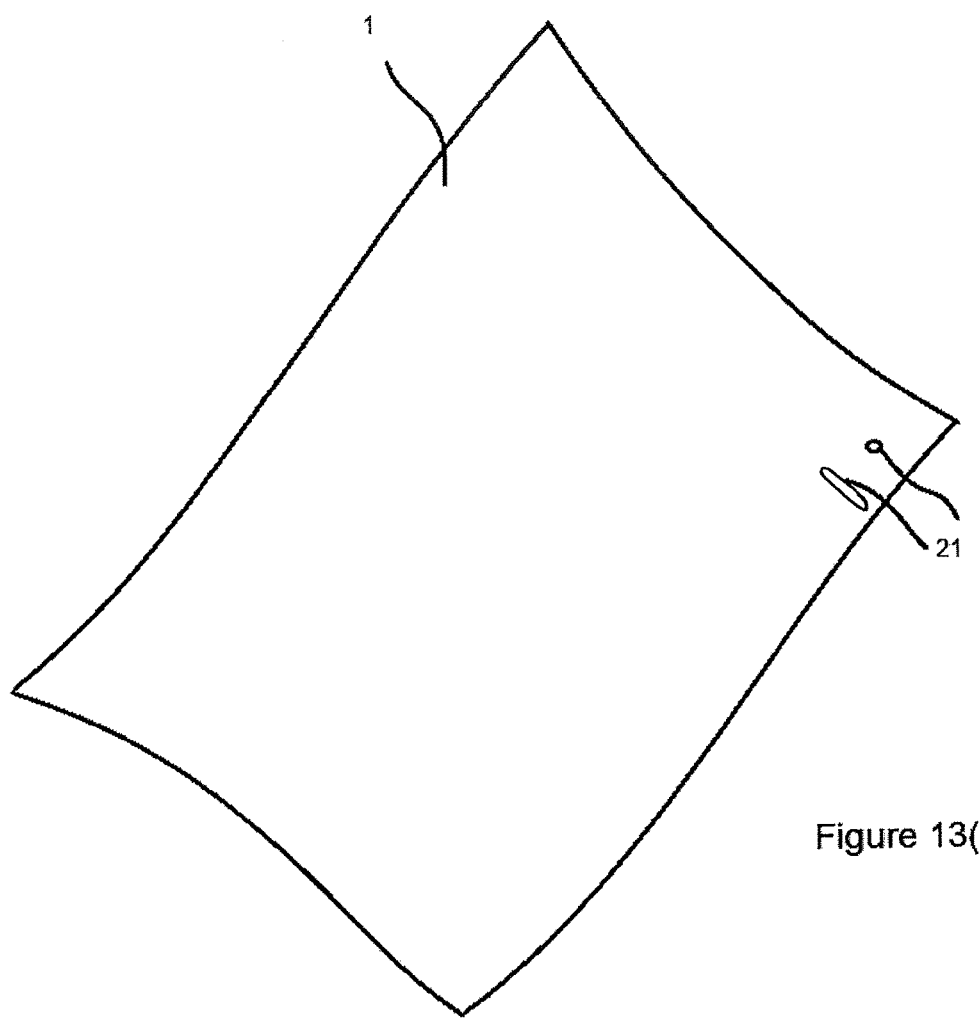

U.S. patent application Ser. No. 13/714,540 (published as US2013/0158568A) describes an automated suture device. The entire disclosure of this application is incorporated herein by reference.

Referring initially to FIGS. 1 and 2 there is illustrated a hernia repair system which comprises a synthetic or biological mesh 1 which is held in place by sutures 2 which are formed by a suture device of the invention. It will be noted that the sutures extend from the internal surface of the body wall and are looped through portion 3 of the wall. The sutures 2 extend in this case only through the peritoneum and the inner facia and the layer of fat tissue therebetween. In addition, the sutures 2 are not tensioned which minimises the force applied to the tissue (and associated pain) whilst ensuring that the mesh 1 is retained in position. As illustrated particularly in FIGS. 3a to 3d of the sutures are applied using a suture device 5 which is manipulated using laparoscopic techniques. In contrast, FIGS. 4a to 4d illustrate the use of conventional tacks to tack the mesh in place.

Referring now to FIGS. 5a and 5b it will be noted that because the suture loops 2 of the invention are substantially tension free expansion and/or contraction of the mesh 1 is readily accommodated. In contrast, in conventional tacking systems (FIGS. 6a, b and 7a, b) expansion/contraction of the mesh results in movement of the tacks with possible risk of dislodgement and/or pain to the patient.

Various hernia repair meshes according to the invention are illustrated in FIGS. 8 to 13. Referring to FIG. 8 in one case a mesh 20 may have a plurality of pre-cut or pre-formed holes 21 which may have a range of configurations, some of which are shown in FIGS. 9a to 9c.

The holes 21 may be used for gripping the mesh to maneuver it into position. The hoes 21 also provide a predefined location for suture insertion.

Referring to FIGS. 13(b) to 13(e) it will be apparent that the holes 21 may be of any suitable size or shape. The hole 21 which can be used to position the mesh using the needle tip may be on the periphery, at one corner and/or at a suitable location in the main body of the mesh. The hole(s) 21 may be made at the time of surgery using a suitable tool such as a punch 22. The punch may be sized to match the needle tip. A punch may be provided as part of a kit for use with a mesh and/or a suturing device of the invention.

Referring to FIGS. 10 and 11 a mesh 25 may be provided with a peripheral band 26 which in this case is of reduced thickness with respect to the main body of the mesh to facilitate needle puncture for suture insertion. Alternatively or additionally, as illustrated in FIGS. 12 and 13 a mesh 27 may have a peripheral band or rim 28 of a material which is softer and more easily penetrated by a needle.

Figure 15:
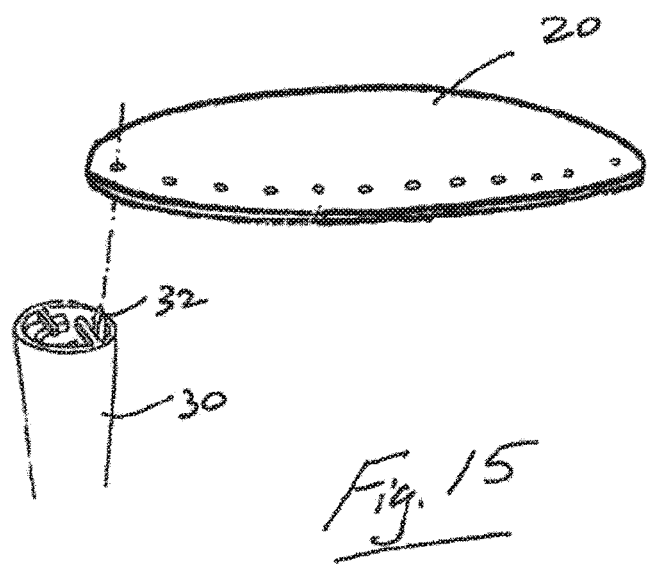
Figure 16:
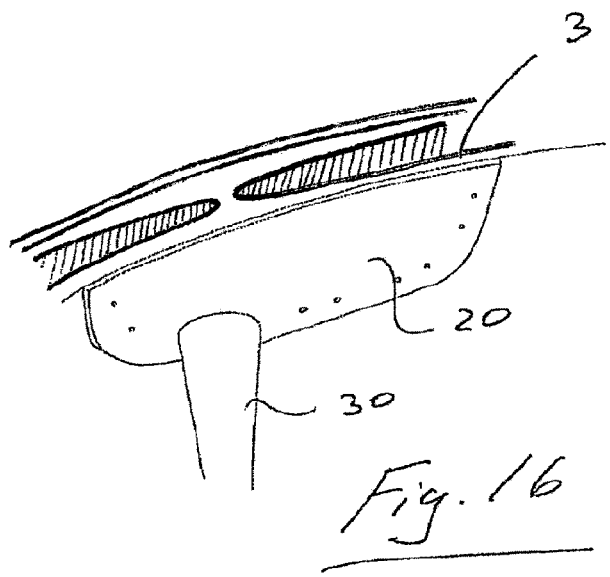
Figure 21A:
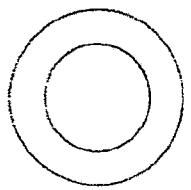
FIGS. 21a to 21f are cross sectional views of various sutures.
Figure 21B:
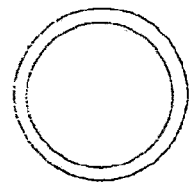
Figure 21C:
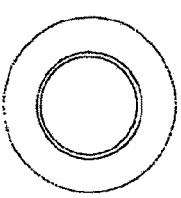
Figure 21D:
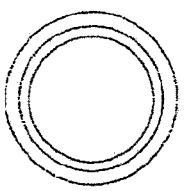
Figure 21E:
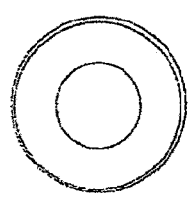
Figure 21F:
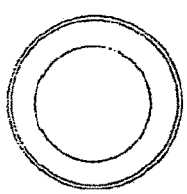

Referring now to FIGS. 14 to 16, in this case a suturing device 30 has a needle 31 with a distal tip 32 which projects beyond the distal end of the shaft of the device. The needle tip 32 may be used to engage the mesh (for example one of the holes 21) to manoeuvre the mesh into position for suturing.

In one case, and referring to FIGS. 17 to 18 (c) a suture device 35 has a retractable shroud 36 to shroud the projecting tip 32 until required for use at the hernia site.

Figure 20:
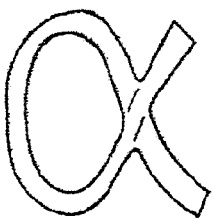
FIGS. 19 and 20 are views of a suture of the invention.
Figure 19:
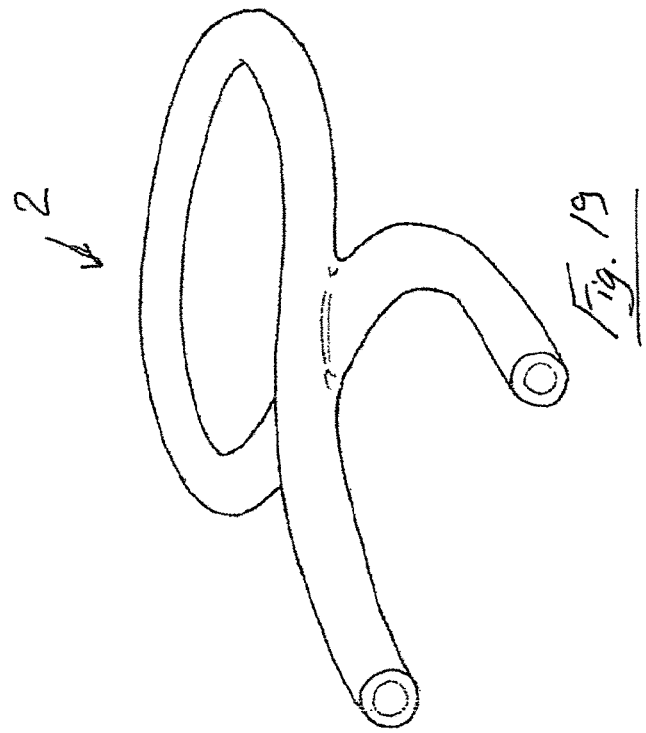

Referring to FIGS. 19 and 20 a suture 2 of the invention is shown in more detail. The suture may be of any desired construction that is suitable for fusing or welding in use. The suture may comprise various layers as illustrated in FIGS. 21(a) to 21(f). Any suitable materials may be used in the various layers such as described in US20130158568A. There may be an inner core, an outer layer and a compatibility layer between the inner core and the outer layer.

A suture device of the invention is illustrated in FIGS. 22(a) to 22(k) in various configurations of use. The suture device comprises a shaft 50 and a needle 52 which creates a curved pathway for delivery of a suture 53. The needle 52 is curved and is rotatably movable from a retracted configuration (FIG. 22a) to an extended configuration for passing through a body wall (FIG. 22b) for threading a suture therethrough (FIGS. 22c to 22e). The suture 53 is accommodated in channels 54, 55 provided in the interior of the shaft of the device. A suture 53 is delivered through a channel 54 to the needle 52 enters and passing through the needle. The suture is then passed through the channel 55. The suture 2 is twisted using a rotary device 56. Cutting elements 57 are used to cut the ends of the suture and a heating device 58 is used to fuse the twisted overlap in the suture (FIG. 22j). The suture device may have retaining or bridging elements 60 to limit collapse of the suture loop. These features 60 ensure that each loop will have the same diameter. They also assist in ensuring alignment of the suture strands in front of the heating element. Thus, the device can be used to form effective sutures even if the device is offset (FIG. 25a, b). The bridging elements 60 are movable into the engaged position for fusing as illustrated in FIG. 22j.

It will be appreciated that the needle can be manufactured in any suitable manner, for example, it may be die cut. In one case the main body of the needle may be of moulded plastics and the tip separately formed (for example die cut) and attached to the main body.

Figure 26:
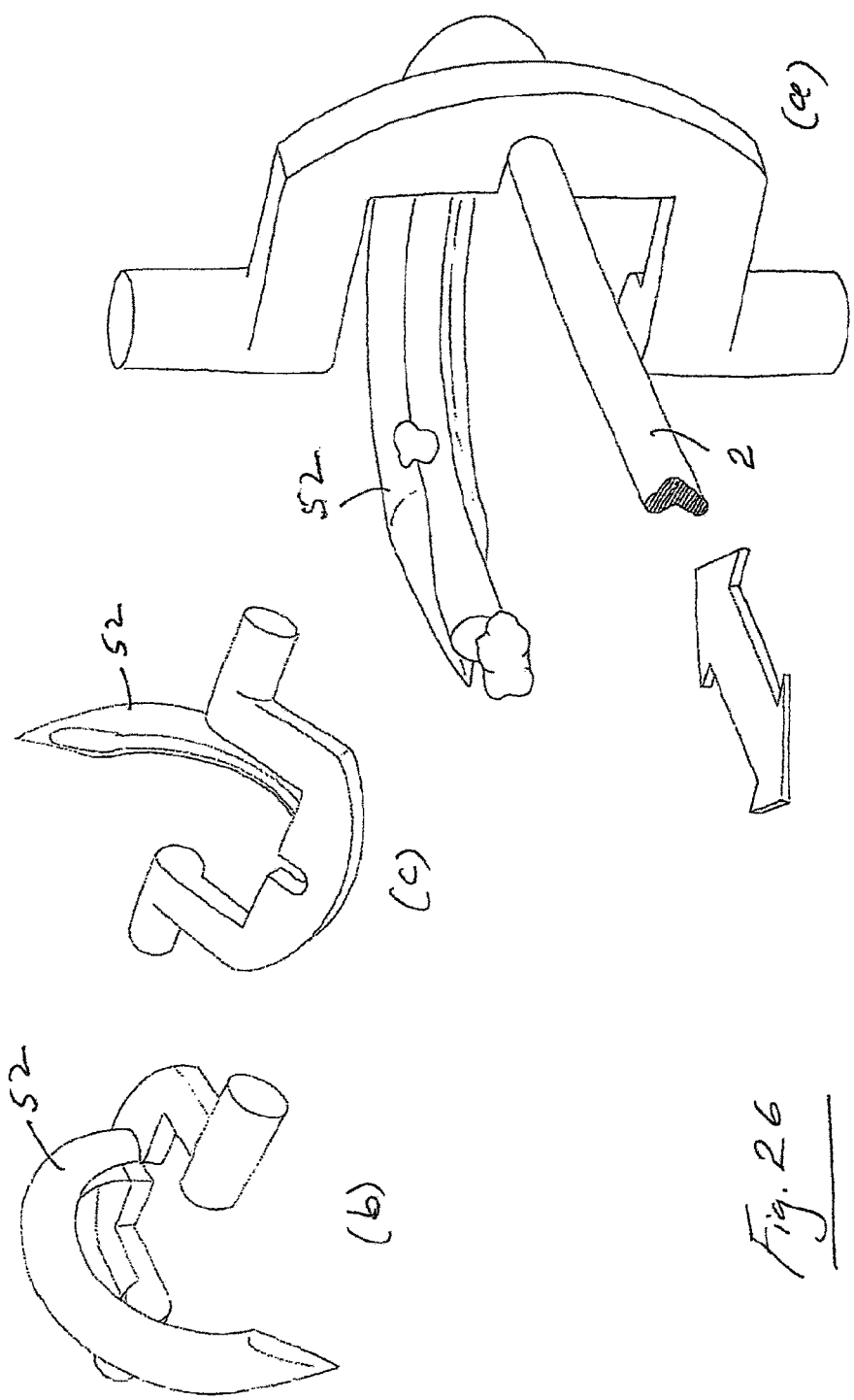
FIGS. 26a to 26c illustrate another suture device according to the invention.
Figure 35:
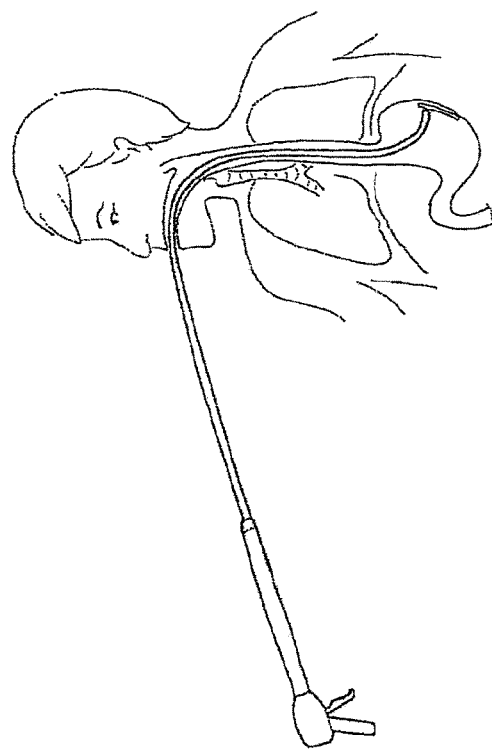
FIG. 35 illustrates a further suture device of the invention.

Referring to FIGS. 26(a) to (c), in advance of passing a suture through the curved needle 52 the pathway through the needle 52 may be flushed, for example by mechanical means such as a wire or fluid to ensure that the pathway is cleared of any extraneous material.

Referring to FIGS. 27 and 28 there is illustrated an alternative suture device 70 in which a suture is accommodated in an external channel 71 in the needle 72. The operation is similar to that of the suture device described in other embodiments.

A suture device 80 with a straight shaft 81 is illustrated in FIGS. 29(a) and 29(b). In this case the distal contact end 82 of the shaft is substantially flat. In some embodiments a contact end 85 is angled for particular applications (FIG. 30). Alternatively or additionally the shaft may have a bend which may be curved (FIG. 31) or more abrupt (FIG. 32). Indeed, for some applications the distal end may be re-directed at any suitable angle such as 90° as illustrated in FIG. 33.

Figure 34:
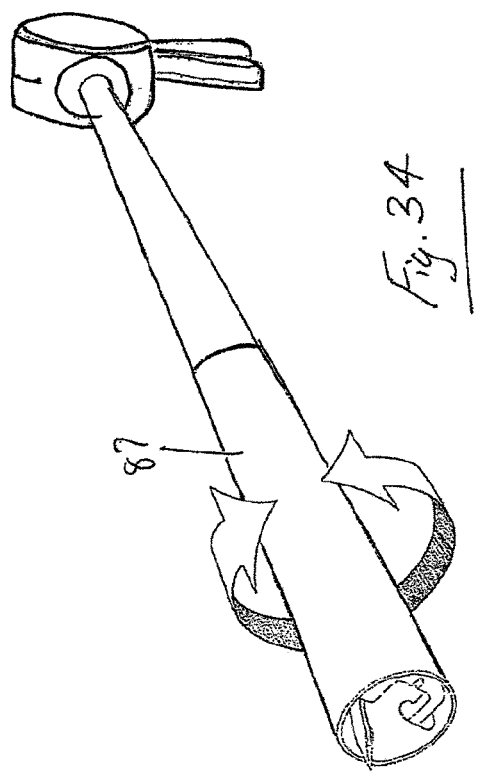
FIG. 34 illustrates another suture device of the invention.

Referring to FIG. 34, in some embodiments a distal end 87 of the shaft may be independently movable (for example rotatable). Alternatively or additionally at least a portion of the shaft may be flexible and/or movable for use in tortuous anatomies to gain access for example through the oesophagus or colon. Various applications of these embodiments are illustrated in FIGS. 36 to 38 by way of example.

Figure 39:
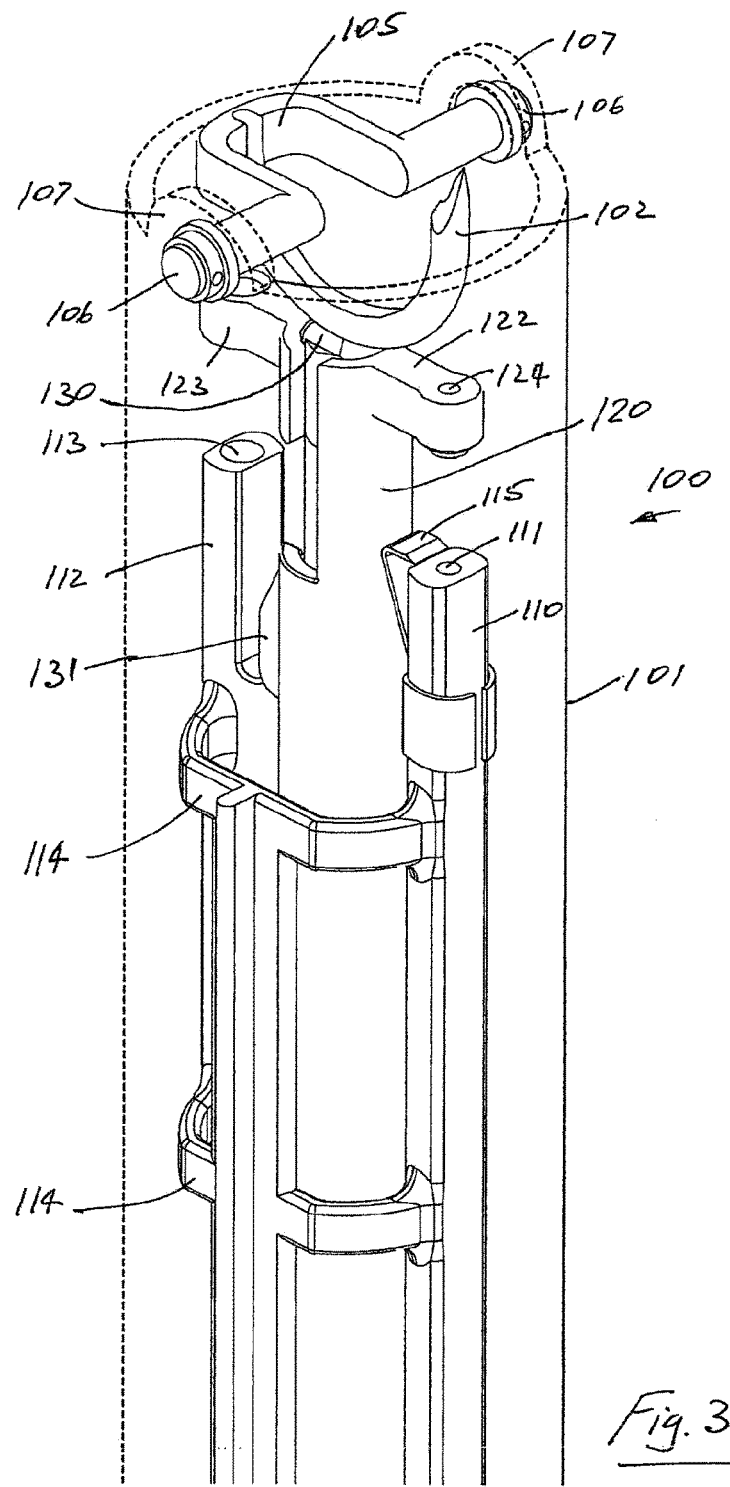
FIG. 39 is a perspective view of portion of another suture device according to the invention.
Figure 40:
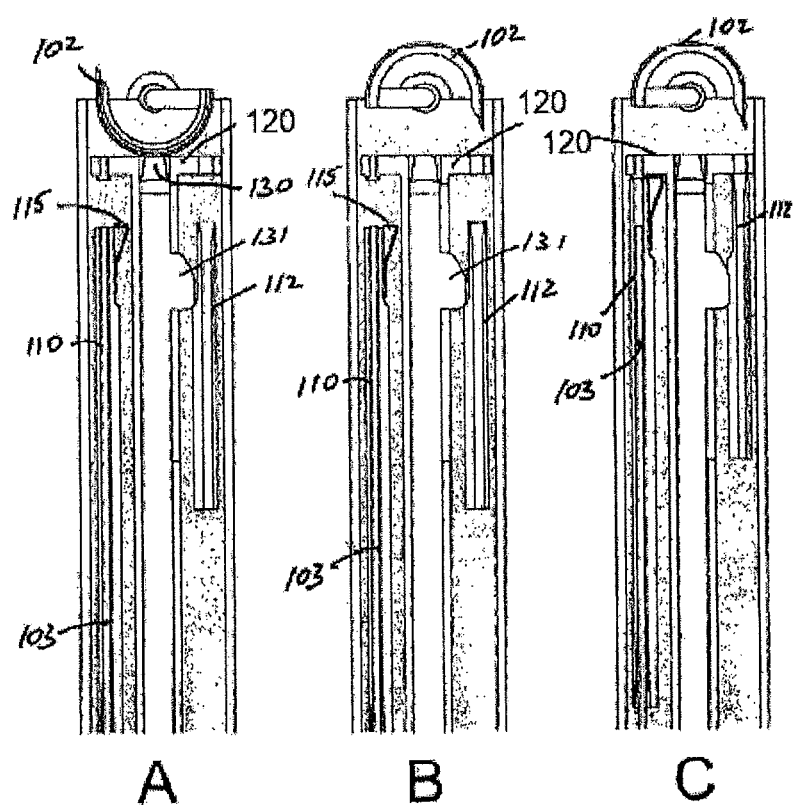
FIGS. 40A to K and 41A to K illustrate the suture device of FIG. 39 in various configurations of use.
Figure 40:
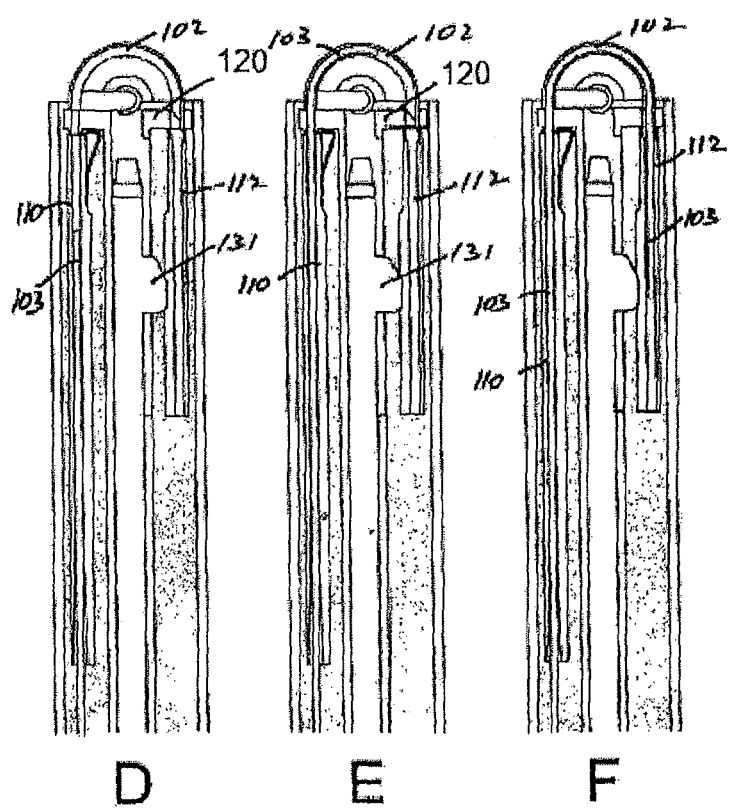
Figure 41:
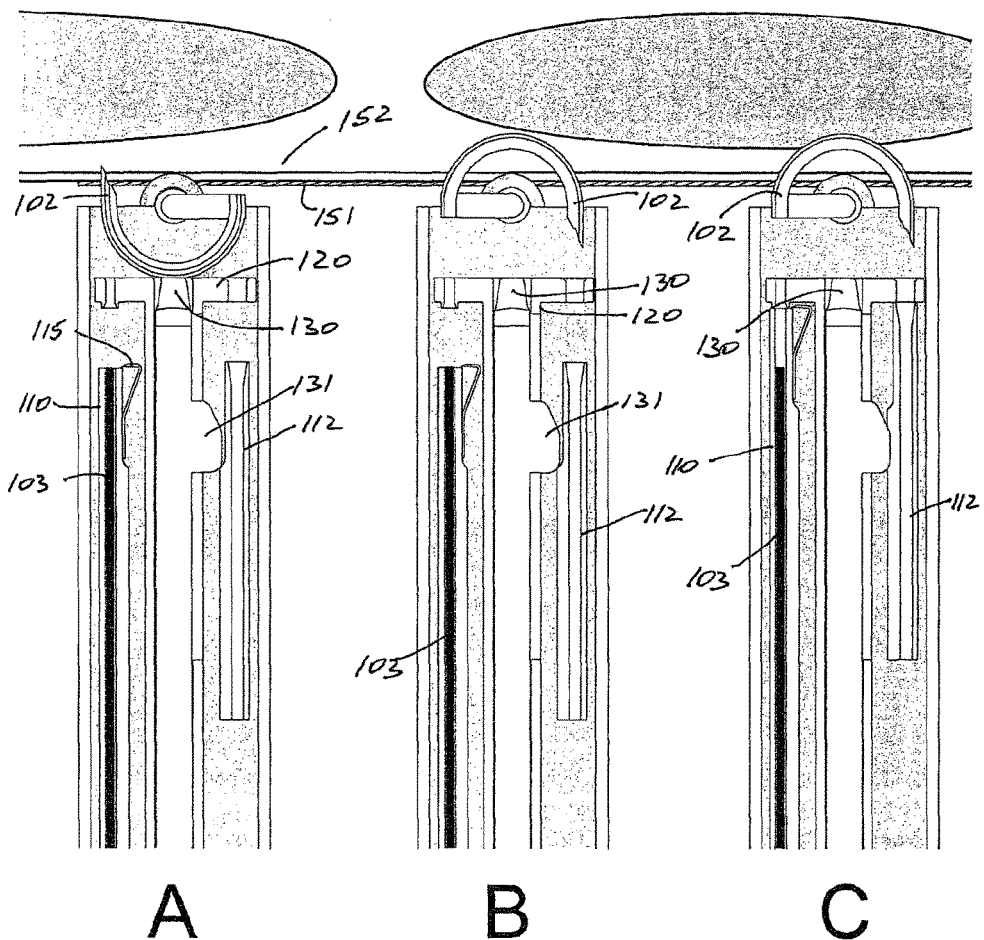
Figure 41:
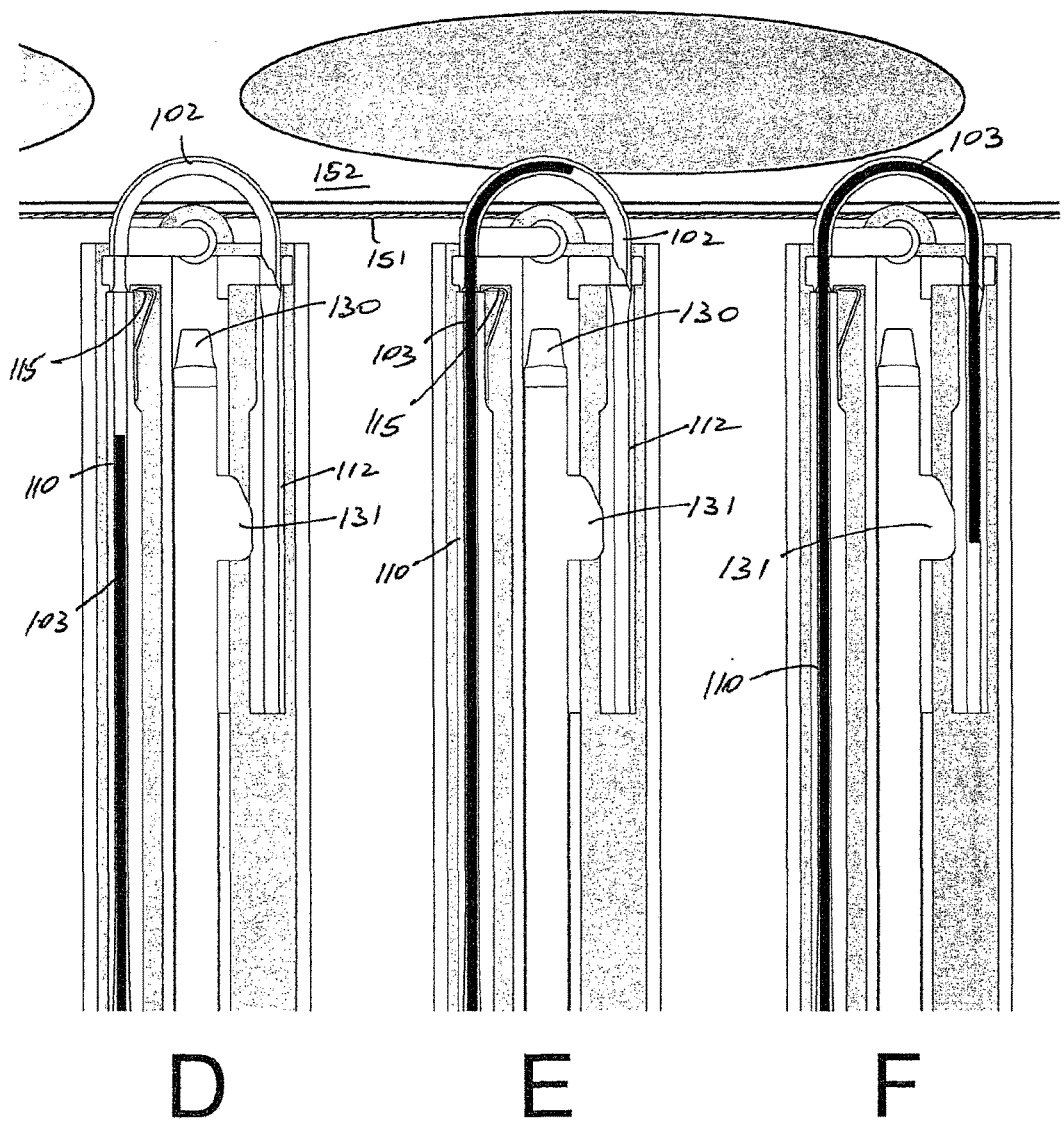
Figure 41:
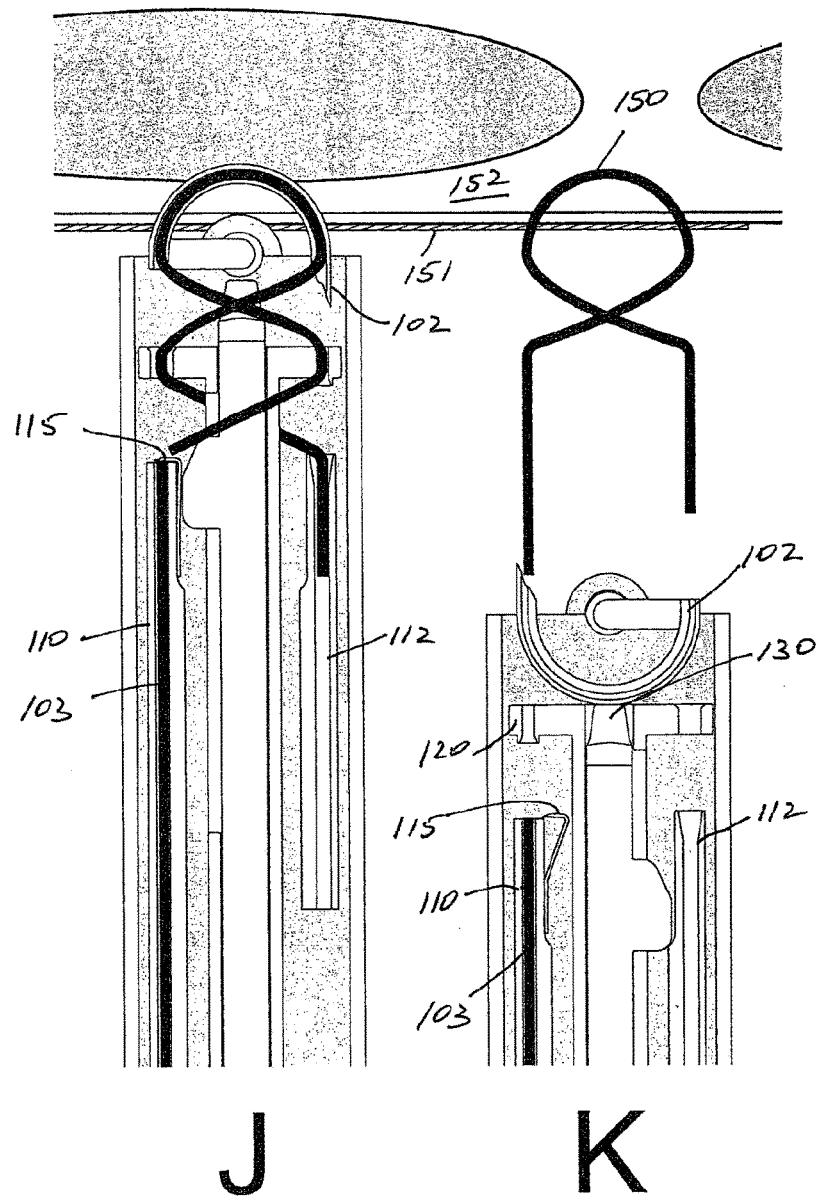

Referring to FIGS. 39 and 40 and 41 there is illustrated another suture device 100 according to the invention. The device 100 comprises a shaft 101 and a needle 102 which creates a curved pathway for delivery of a suture 103. The needle 102 is curved and is fixed to a U-shaped mounting bracket 105 which is rotatably mounted by pivot pins 106 in receivers 107 adjacent to the distal end of the shaft 101. The curved needle 102 is rotatably movable from a retracted (FIG. 40/41A) to an extended configuration (FIG. 40/41B).

The suture 103 is housed in a feed channel 110 within the shaft 101. The feed channel 110 has an open distal end 111. The shaft 101 also houses a suture receiving channel 112 with an open distal end 113. The channels 110 and 112 are in this case interconnected by connecting arms 114 and may be provided by a single component.

It will be noted that the open distal end 113 of the suture receiving channel 112 is in this case larger than the open distal end of the suture feed channel 110. This facilitates entry of the suture 103 into the receiving channel 112, even if the suture 103 is out of alignment with the distal end 113 of the receiving channel 112.

A suture cutter 115 is located adjacent to the suture feed channel distal end 111 for cutting the suture 103, when required. The cutting element 115 may be spring biased to return to a rest (non-cutting) position. In this case the cutting element 115 is provided by an angle shaped strip of spring steel material or the like.

The device also comprises a rotatable twisting element 120 having a rotating shaft 121 and a pair of radially extending arms 122, 123, having through suture-receiving through holes 124, 125. A heating rod in the form of a heating element 130 is also provided to heat meld a twist 135 when formed in the suture 103. The heating rod 130 is axially movable with respect to the twisting element 120. The heating rod 130 also has a radially extending projection 131.

The operation of the device is illustrated in FIGS. 40/41A to 40/41K. In FIG. 40/41A the device is ready to operate. The curved needle 102 with the open receiving channel is aligned with the tip of the needle facing the mesh and tissue to which the mesh is to be applied. In FIG. 40/41B the needle 102 is rotated to penetrate tissue and form a loop through the tissue. In this configuration the suture receiving channel in the needle is aligned with the suture feed channel distal end 111.

In FIG. 40/41C the suture feed channel 110 is advanced so that the distal end 111 is aligned with the feed hole 124 in the suture twisting device 120 and the distal end 113 of the suture receiving channel 112 is aligned with the receiving hole 125 in the suture twisting device 122.

FIG. 40/41D shows the twisting device 120 advanced by the feed and receiving channels 110, 112 towards the needle 102. The suture 103 is then advanced through the feed channel 110 and through the open channel in the needle (FIG. 40/41E) and into the suture capture channel 112 (FIG. 40/41F).

The suture twisting element 120 is then retracted (FIG. 40/41G) followed by further retraction of the feed and receiving channels 110, 112 (FIG. 40/41H). FIG. 40/41I illustrates the rotation of the twisting device 120 to form a twist 135 in the suture.

The heating rod 130 is then advanced relative to the twisting device 120 (FIG. 40/41J) to heat meld the twist 135 in the suture 103. The advancing of the heating rod 130 also causes the projection 131 to engage the cutting element 115 which pivots to automatically cut the suture 103.

FIG. 40/41K shows the suture twisting device 120 returned to the untwisted configuration and the needle 102 retracted, leaving a completed suture 150 in place.

FIG. 41A to K illustrate the device being used to suture a mesh to a body wall. FIG. 41K shows a completed suture 150 looped through mesh 151 and tissue 152.

The needle 102 is of arcuate shape and comprises an open suture-receiving channel. The needle suture-receiving channel may for example be of generally U-shaped in transverse cross section. The open suture channel in the needle 102 facilitates formation of a twist in the suture to form a loop whilst allowing the formed loop to be released from the suture device when the needle is moved into the retracted configuration illustrated for example in FIGS. 40K and 41K.

FIGS. 42a and b illustrate a needle operating system with operating elements 140 linked back to an operating handle or lever 141 at the proximal end. The operating elements 140 may comprise, pulleys, wires or the like. In this case the diameter of the handle shaft 142 is larger, for example twice as large as the diameter of the rotatable shaft 106 of the needle 102. The handle/lever 141 is rotated by the surgeon at a 1:2 ratio with the needle 102 which gives the surgeon full control over the movement of the needle 102 and immediate feedback at the proximal end.

In the invention individual suture loops are formed to secure a mesh to adjacent tissue. The loops will generally all be of a pre-set size set by the suture device. The suture loops ensure that the mesh is efficiently and effectively placed and retained in place but with sufficient flexibility to allow some movement of the mesh to accommodate patient movement, for example as a result of coughing. Unlike anchors or screws the loops will not result in localised pain to the patient when such movement occurs. The loops are generally slack and not tensionsed against tissue. The mesh may be applied in any desired manner, for example, by first applying loops at some locations such as the corners to locally retain the mesh and then apply further suture loops around the periphery of the mesh.

As described above, the loop may extend through just one or two holes in the mesh. The holes may be pre-formed in the mesh or may be made when the curved needle is advanced through the mesh before the suture is threaded through the needle.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiment hereinbefore described which may be varied in construction and detail.

The invention claimed is:
1. A method for repairing a hernia comprising the steps of:
providing a suture device;
providing a mesh;
laparoscopically delivering the mesh to the site of the hernia;
delivering the suture device to the site of the hernia; and
laparoscopically suturing the mesh with a plurality of individual sutures to an internal body wall at the site of the hernia,
wherein each of the sutures comprises a closed loop which extends through the mesh, into the body wall and out of the body wall, and the individual sutures are not tensioned such that a force applied to the internal body wall is minimized while ensuring that the mesh is retained at the site of the hernia, and
wherein the suture device comprises:
a shaft including a suture feed channel and a suture return channel;
a needle at a distal end of the shaft that creates a curved pathway for delivery of the sutures through a portion of the internal body wall;
a rotary device for twisting the sutures to form the closed loops, the rotary device having a suture receiving hole and a suture return hole, the rotary device being rotatable from a receiving configuration in which the suture receiving hole and the suture return hole are in alignment with the suture feed channel and the suture return channel, respectively, to a twisted configuration in which the suture receiving hole and the suture return hole are in alignment with the suture return channel and the suture feed channel, respectively; and a closure device for closing the suture to form the closed loop.

2. The method as claimed in claim 1 wherein the closed loop is adapted to facilitate movement of the mesh relative to the body wall.

3. The method as claimed in claim 1 wherein the mesh has a plurality of holes provided therein to receive the sutures.

4. The method as claimed in claim 3 wherein the plurality of holes are provided around at least a portion of the periphery of the mesh.

5. The method as claimed in claim 4 wherein the peripheral portion is softer with respect to the main mesh body of the mesh.

6. The method as claimed in claim 1 wherein the needle is of an arcuate shape, and is movable from a retracted configuration at least partially within the shaft to an extended configuration for passing through portion of the internal body wall, and the needle is rotatably movable between the retracted and the extended configuration.

7. The method as claimed in claim 1 wherein the needle comprises an open suture-receiving channel.

8. The method as claimed in claim 7 wherein the suture-receiving channel has a transverse cross section which is generally U-shaped.

9. The method as claimed in claim 1 wherein the closure device comprises a heating device for fusing the sutures.

10. The method as claimed in claim 1 further comprising a cutting device for cutting the sutures.

11. The method as claimed in claim 1 further comprising a fusing element for fusing a twist in the sutures; and a suture cutting element for cutting the twisted sutures.

12. The method as claimed in claim 11 further comprising a retainer for stabilizing the sutures during cutting and/or fusing.

* * * * *